(12) United States Patent
An et al.

(10) Patent No.: US 8,735,129 B2
(45) Date of Patent: May 27, 2014

(54) **GINSENOSIDE GLYCOSIDASE DERIVED FROM THE GENUS *TERRABACTER*, AND USE THEREOF**

(75) Inventors: Dong Shan An, Daejeon (KR); Song Gun Kim, Daejeon (KR); Sung Taik Lee, Daejeon (KR); Wan Taek Im, Daejeon (KR); Hyung Gwan Lee, Daejeon (KR); Sun Chang Kim, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/453,893

(22) Filed: Apr. 23, 2012

(65) Prior Publication Data

US 2012/0264167 A1 Oct. 18, 2012

Related U.S. Application Data

(63) Continuation-in-part of application No. PCT/KR2010/007338, filed on Oct. 25, 2010.

(30) Foreign Application Priority Data

Oct. 23, 2009 (KR) ........................ 10-2009-0101469

(51) Int. Cl.
*C12N 9/24* (2006.01)
*C12P 33/20* (2006.01)
*C12N 1/20* (2006.01)
*C12N 15/00* (2006.01)

(52) U.S. Cl.
USPC ..... 435/200; 435/53; 435/320.1; 435/252.33; 536/23.2

(58) Field of Classification Search
None
See application file for complete search history.

(56) References Cited

FOREIGN PATENT DOCUMENTS

CN 101100659 A * 1/2009

OTHER PUBLICATIONS

Yan, Q. et al. "Purification and properties of a novel beta-glucosidase, hydrolyzing ginsenoside Rb1 to CK, from Paecilomyces Bainier," Journal of Microbiology and Biotechnology. vol. 18(6), pp. 1081-1089, 2008.
Cheng, L. Q. et al. "Conversion of major ginsenoside Rb1 to 20(S)-ginsenoside Rg3 by Microbacterium sp. GS514," Phytochemistry. vol. 69(1), pp. 218-224, 2008.
Cheng, L. Q. et al. "Microbial conversion of ginsenoside Rb1 to minor ginsenoside F2 and gypenoside XVII by intrasporangium sp. GS603 isolated from soil," Journal of Microbiology and Biotechnology. vol. 17(12), pp. 1937-1943, 2007.
Yu, H. et al. "Purification and characterization of new special ginsenosidase hydrolyzing multiglycisides of protopanaxadiol ginsenosides, ginsenosidase type I," Chemical and Pharmaceutical Bulletin. vol. 55(2), pp. 231-235, 2007.
Perez-Pons, J. A. et al. "A beta-glucosidase gene(bg13) from Streptomyces sp. strain QM-B814. Molecular cloning, nucleotide sequence, purification and characterization of the encoded enzyme, a new member of family 1 glycosyl hydlolases," European Journal of Biochemistry. vol. 223(2), pp. 557-565, 1994.
An, D. S. et al. "Identification and characterization of a novel Terrabacter gingenosidimutans sp.nov.beta-glucosidase that transforms ginsenoside Rb1 into the rare gypenosides XVII and LXXV," Applied and Environmental Microbiology. vol. 76, pp. 5827-5836, 2010.
Korea Patent Abstracts for publication No. KR 1020000062140, published Oct. 25, 2000, five pages.
Korea Patent Abstract for publication No. 1020020029138 A, published Apr. 18, 2002, 18 pages.
Korea Patent Abstract for publication No. 1020090065933 A, published Jun. 23, 2009, 15 pages.

* cited by examiner

*Primary Examiner* — Iqbal H Chowdhury
(74) *Attorney, Agent, or Firm* — Cooley LLP

(57) ABSTRACT

The present invention relates to a novel ginsenoside glycosidase protein derived from the genus *Terrabacter*, the protein having an activity of converting protopanaxadiol (PPD)-type saponins into highly active substances, which can be absorbed inside the body, by selective hydrolysis of a particular bond of ginsenoside. More specifically, the present invention relates to an amino acid sequence of the protein, a nucleic acid sequence encoding the protein, a recombinant vector comprising the nucleic acid sequence, and a transformant transformed with the vector, and a method for producing ginsenoside glycosidase derived from the genus *Terrabacter* by culturing the transformant, a method for converting PPD-type major saponins into the minor saponin forms using the protein, and a composition for converting PPD-type saponins into soluble saponins, comprising the protein as an active component.

9 Claims, 16 Drawing Sheets

SEQUENCE LISTING

<160> NUMBER OF SEQ ID NOS: 8

<210> SEQ ID NO 1
<211> LENGTH: 589
<212> TYPE: PRT
<213> ORGANISM: Terrebacter sp.
<220> FEATURE:
<221> NAME/KEY: PEPTIDE
<222> LOCATION: (1)..(589)
<223> OTHER INFORMATION: amino acid sequence of Bgl-gyp17

<400> SEQUENCE: 1

```
Met Asp Pro Tyr Glu Asp Pro Arg Leu Pro Val Glu Val Arg Val Glu
 1               5                  10                  15

Asp Leu Leu Gly Arg Leu Ser Leu Glu Glu Lys Val Gly Leu Met Phe
            20                  25                  30

Gln Thr Val Ile Glu Ala Gly Ser Asp Gly Thr Val Leu Glu His Pro
        35                  40                  45

Gly Ser Ile Ser Lys Ser Pro Thr Ser Thr Val Val Leu Asp Lys His
    50                  55                  60

Leu Thr His Phe Asn Val His Ala Leu Asp Asp Pro Arg Met Ala Ala
65                  70                  75                  80

Arg Trp Ser Asn Ala Leu Gln Ala Leu Ala Glu Arg Thr Pro His Gly
                85                  90                  95

Ile Pro Val Thr Val Ser Thr Asp Pro Arg His Ala Phe Ile Glu Asn
            100                 105                 110

Val Gly Val Ser Phe Ser Ala Gly Ala Phe Ser Gln Trp Pro Glu Pro
        115                 120                 125

Leu Gly Leu Ala Ala Leu Arg Asp Ala Asp Ala Val Arg Arg Phe Ala
    130                 135                 140

Asp Ile Ala Arg Gln Glu Tyr Val Ala Val Gly Ile Arg Ala Ala Leu
145                 150                 155                 160

His Pro Thr Leu Asp Leu Ala Thr Glu Pro Arg Trp Ala Arg Gln Ala
                165                 170                 175

Gly Thr Phe Gly Gln Asp Pro Asp Leu Val Thr Glu Leu Gly Val Ala
            180                 185                 190

Tyr Leu Lys Gly Phe Gln Gly Asp Ser Leu Gly Ser Gly Ser Val Ala
        195                 200                 205

Cys Thr Ser Lys His Phe Pro Gly Gly Pro Gln Lys Asp Gly Glu
    210                 215                 220

Asp Ala His Phe Pro Tyr Gly Arg Glu Gln Val Tyr Pro Gly Gly Arg
225                 230                 235                 240

Phe Ala Asp His Leu Lys Pro Phe Pro Pro Ile Ile Glu Ala Gly Thr
                245                 250                 255

Ala Gly Ile Met Pro Tyr Tyr Gly Met Pro Val Asp Leu Val Val Asp
```

```
                    260                 265                 270
Gly Val Glu Ile Glu Pro Ile Gly Phe Gly Tyr Asn Lys Gln Val Val
            275                 280                 285

Thr Gly Leu Leu Arg Glu Lys Leu Gly Tyr Asp Gly Val Val Val Thr
        290                 295                 300

Asp Trp Glu Leu Val Asn Asp Asn His Val Gly Asp Gln Val Leu Pro
305                 310                 315                 320

Ala Arg Ala Trp Gly Val Glu His Leu Asp Pro His Gly Arg Met Glu
                325                 330                 335

Leu Ile Leu Glu Ala Gly Ala Asp Gln Phe Gly Gly Glu Glu Cys Val
            340                 345                 350

Glu Ile Leu Leu Asp Leu Val Ala Gln Gly Arg Val Thr Glu Ala Arg
        355                 360                 365

Val Asp Glu Ser Ala Arg Arg Ile Leu Ala Val Lys Phe Arg Leu Gly
    370                 375                 380

Leu Phe Glu Asn Pro Tyr Val Asp Glu Asp Ala Ala Ala Thr Val
385                 390                 395                 400

Gly Arg Asp Asp Phe Arg Glu Glu Gly Tyr Ala Ala Gln Ala Arg Ser
                405                 410                 415

Val Thr Val Leu His His Glu Gly Gly Arg Leu Pro Leu Glu His Gly
            420                 425                 430

Leu Arg Ile Tyr Ala Glu Gln Val Ser Pro Glu Ala Val Ala Arg His
        435                 440                 445

Gly Lys Leu Val Asp Arg Pro Glu Asp Ala Asp Val Ala Val Val Arg
    450                 455                 460

Leu Thr Ala Pro Phe Asp Pro Arg Ser Asp Leu Phe Leu Glu Ser Trp
465                 470                 475                 480

Phe His Gln Gly Ser Leu Asp Phe Pro Pro Gly Leu Val Ala Arg Leu
                485                 490                 495

Glu Arg Ile Ala Ala Val Cys Pro Leu Val Val Asp Val Leu Asp
            500                 505                 510

Arg Pro Ala Val Leu Thr Pro Leu Leu Arg Phe Ala Ser Ala Val Val
        515                 520                 525

Gly Ser Phe Gly Ser Cys Asp Asp Ala Leu Leu Asp Ala Leu Thr Gly
    530                 535                 540

Thr Ile Ala Pro Val Gly Arg Leu Pro Phe Asp Leu Pro Arg Ser Met
545                 550                 555                 560

Asp Gln Val Arg Ala His Gly Glu Asp Val Pro Gly Tyr Asp Asp Pro
                565                 570                 575

Leu Phe Pro Phe Gly His Gly Leu Arg Leu Asp Thr Glu
            580                 585

<210> SEQ ID NO 2
<211> LENGTH: 1770
<212> TYPE: DNA
<213> ORGANISM: Terrebacter sp.
<220> FEATURE:
<221> NAME/KEY: gene
<222> LOCATION: (1)..(1770)
<223> OTHER INFORMATION: DNA sequence of bgl-gyp17

<400> SEQUENCE: 2
atggatccct acgaggaccc ccggctcccc gtagaggtgc gcgtcgagga cctgctcggt     60
cggctctcgc tcgaggagaa ggtcggcctg atgttccaga ccgtcatcga ggccggctcg    120
gacggcacgg tgctcgagca ccccggcagc atcagcaagt cgccgacgag cacggtcgtg    180
```

| | |
|---|---|
| ctcgacaagc acctcacgca cttcaacgtc cacgcgctcg acgacccgcg gatggcggcc | 240 |
| aggtggagca acgccctgca ggcactggcc gagcgcacgc cacacggcat acccgtgacg | 300 |
| gtgtcgacag acccgcgtca cgcgttcatc gagaacgtcg gggtgtcctt ctccgcaggc | 360 |
| gcgttctcgc agtggcccga gccgctcggc ctcgcggcgc tccggacgcg ggacgccgtg | 420 |
| cgacgcttcg ccgacatcgc ccgccaggag tacgtcgcgg tgggcatccg tgccgcactg | 480 |
| cacccgaccc tggacctcgc gaccgagccg cgctgggccc gccaggccgg caccttcggc | 540 |
| caggatcccg acctcgtgac cgagctcggt gtcgcctatc tcaagggttt ccaaggggat | 600 |
| tcgctcgggct ccggcagcgt ggcgtgcacg agcaagcact tccccggcgg cggcccccag | 660 |
| aaggacggcg aggacgcgca cttcccctac ggccgcgagc aggtctatcc cggtgggcgt | 720 |
| ttcgccgacc acctcaagcc gttcccgccg atcatcgagg ccggcaccgc ggggatcatg | 780 |
| ccctactacg gcatgccggt cgacctcgtc gtcgacggcg tcgagatcga gccgatcggc | 840 |
| ttcggctaca acaagcaggt ggtcaccggg ctgctccgcg agaagctcgg ctacgacggc | 900 |
| gtcgtcgtca cggactggga gctcgtcaac gacaaccacg tcggagacca ggtgctgccc | 960 |
| gcccgcgcct ggggcgtcga gcacctcgac ccgcacggcc gcatggagct catcctcgag | 1020 |
| gccggcgccg accagttcgg tggcgaggag tgcgtcgaga tcctgctcga cctcgtcgcg | 1080 |
| caggggcgcg tcaccgaggc tcgcgtcgac gagtcggccc gccgcatcct ggcggtgaag | 1140 |
| ttccgtctcg gcctcttcga gaacccctac gtcgacgagg acgaggccgc ggcgacggtc | 1200 |
| gggcgcgacg acttccgcga ggaggggtat gccgcgcagg cccgttcggt gaccgtgctg | 1260 |
| caccacgagg gtggccggct gccgctcgag catggcctgc gcatctacgc cgagcaggtc | 1320 |
| tcacccgagg cggtcgcccg gcacggcaag ctcgtcgacc ggcccgagga cgccgacgtc | 1380 |
| gcggtcgtgc gcctgacggc gccgttcgac ccgcgctcgg acctcttcct cgagtcgtgg | 1440 |
| ttccaccagg gctcgctcga cttcccgccc ggcctcgtcg cccgcctcga gcggatcgcc | 1500 |
| gcggtgtgcc cgctcgtcgt cgacgtcgtg ctcgaccggc cggccgtcct cacccccgctg | 1560 |
| ctgcgcttcg cgtccgcggt cgtcggcagc ttcggctcgt gcgacgacgc cctgctcgac | 1620 |
| gccctcaccg gcaccatcgc gcccgtgggc cgtctgccgt cgacctgcc ccgttcgatg | 1680 |
| gatcaggtgc gcgcacacgg cgaggacgtc ccgggctacg acgacccgct cttccccttc | 1740 |
| ggccacgggc ttcgtctcga cacggagtga | 1770 |

<210> SEQ ID NO 3
<211> LENGTH: 20
<212> TYPE: DNA
<213> ORGANISM: Artificial Sequence
<220> FEATURE:
<223> OTHER INFORMATION: 27F universal primer

<400> SEQUENCE: 3
agagtttgat cmtggctcag                                              20

<210> SEQ ID NO 4
<211> LENGTH: 22
<212> TYPE: DNA
<213> ORGANISM: Artificial Sequence
<220> FEATURE:
<223> OTHER INFORMATION: 1492R universal primer

<400> SEQUENCE: 4
tacggytacc ttgttacgac tt                                           22

<210> SEQ ID NO 5

-continued

```
<211> LENGTH: 21
<212> TYPE: DNA
<213> ORGANISM: Artificial Sequence
<220> FEATURE:
<223> OTHER INFORMATION: primer for FP-1

<400> SEQUENCE: 5
ctggtccacc tacaacaaag g                                                   21

<210> SEQ ID NO 6
<211> LENGTH: 22
<212> TYPE: DNA
<213> ORGANISM: Artificial Sequence
<220> FEATURE:
<223> OTHER INFORMATION: primer for RP-1

<400> SEQUENCE: 6
agagattttg agacaggatc cg                                                  22

<210> SEQ ID NO 7
<211> LENGTH: 29
<212> TYPE: DNA
<213> ORGANISM: Artificial Sequence
<220> FEATURE:
<223> OTHER INFORMATION: forward primer for pbgl-gin18

<400> SEQUENCE: 7
cggaattcat ggatccctac gaggacccc                                           29

<210> SEQ ID NO 8
<211> LENGTH: 27
<212> TYPE: DNA
<213> ORGANISM: Artificial Sequence
<220> FEATURE:
<223> OTHER INFORMATION: reverse primer for pbgl-gin18

<400> SEQUENCE: 8
cccaagctta ccccgggacg acgaggc                                             27
```

US 8,735,129 B2

GINSENOSIDE GLYCOSIDASE DERIVED FROM THE GENUS *TERRABACTER*, AND USE THEREOF

CROSS-REFERENCES TO RELATED APPLICATIONS

This application is a continuation-in-part of International PCT Patent Application No. PCT/KR2010/007338, which was filed on Oct. 25, 2010, which claims priority to Korean Patent Application No. 10-2009-0101469, filed Oct. 23, 2009. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_009_01US_ST25.txt. The text file is 9 KB, was created on Apr. 23, 2012, and is being submitted electronically via EFS-Web.

TECHNICAL FIELD

The present invention relates to a novel ginsenoside glycosidase protein derived from the genus *Terrabacter*, an amino acid sequence constituting the protein, a nucleic acid sequence encoding the protein, a recombinant vector comprising the nucleic acid sequence, a transformant transformed with the vector, a method for preparing ginsenoside glycosidase derived from the genus *Terrabacter* by culturing the transformant, and a composition for converting protopanaxadiol (PPD)-type saponins into in vivo absorbable, soluble saponins by using the protein.

BACKGROUND ART

Saponins, glycosides widely distributed in the plant kingdom, include diverse ring compounds formed by the non-sugar portion. A saponin, contained in ginseng or red ginseng as a major physiologically active ingredient, is called ginsenoside which means ginseng glycoside, named to distinguish it from other vegetables' saponin based on it's different chemical structure.

Ginsenosides are classified into three groups based on their aglycone structure: Protopanaxadiol (PPD)-type ginsenosides, Protopanaxatriol (PPT)-type ginsenosides, and Oleanolic acid-type ginsenosides. These three groups are further classified based on the position and number of sugar moieties (aglycones) attached by a glycosidic bond at C-3, C-6, and C-20 positions of the rings in the chemical structure. Among them, Rg1, Re, Rb1, Rc and Rb2 are major ginsenosides that account for over 90% of total ginsenoside content (Park, 2004), but show a very low in vivo absorption when orally administered into the human body, because of their large size. Therefore, deglycosylation of major ginsenosides is required in order to show effective physiological activities in vivo (Tawab et al., 2003; Akao et al., 1998).

In recent decades, excellent pharmacological effects of minor ginsenosides such as Rg3, Rh2 and compound K have been revealed. These recent studies have brought more attention to minor ginsenosides having superior pharmacological effects, such as F2, Rg3, Rh1, Rh2, and compound K (C—K), and there is a need to develop a method for increasing the content ratio of particular minor ginsenosides.

Among them, the protopanaxadiol-type ginsenosides, Rh1 and Rh2 are reported to strongly induce the differentiation of F9 teratocarcinoma stem cells (F9 teratocarcinoma) (Lee et al., Proc. $6^{th}$, Intl. Ginseng symp., 127, 1993), and they are also reported to show strong inhibitory effects on the proliferation of various tumor cells such as B16 melanoma, MK-1 (stomach cancer cell) (Matsunaga et al., Chem, Pharm. Bull., 38, 3480, 1990) and ovarian cancer cell (HRA) (Kikuchi et al., Anticancer Drugs. England., 2, 63, 1991). Rh2 has such excellent pharmacological effects, but is present in red ginseng in only trace amounts. Even though methods for the mass-production of Rh2 have been actively studied, effective methods have not been established yet.

Regarding the ginsenoside F2, F2 has been known as an ingredient having the effects of suppressing the proliferation of tumor cells and reversing multi-drug resistance in tumor cells and bacteria (Sung et al., Korean Journal of Pharmacognosy 28(1), 35, 1997). It is known that ginseng saponins are metabolized by intestinal flora such as Prevotellaris after they are orally administered, and their metabolite F2 shows pharmaceutical effects. However, useful F2 is also present only in small amounts in some ginsengs, and thus it is difficult to produce a large amount thereof. In addition, it is difficult to produce only high-purity F2 because of the production of various secondary metabolites during the metabolic process.

For the production of minor ginsenosides that are present in a small amount, chemical decomposition (De Mayo et al., canad. J. Chem., 43, 2033, 1965), enzymatic method (Kitagawa et al., Terahedron Letters, 30, 2283, 1974), and glycoside synthesis (Korean Patent No. 10-2005-0007250) have been suggested, but these methods have limitations on mass-production such as 1) the many production steps required for the production process, 2) the loss of desired compounds during processing, 3) the use of inedible catalysts, or 4) low yield.

In particular, enzymes such as ginsenoside glycosidase, α-L-arabinopyranosidase, α-L-arabinofuranosidase, and α-L-rhamnosidase can be used in the enzymatic method, and there have been many studies on the biotransformation of major ginsenosides such Rb1, Rb2, Rc, and Re using these enzymes. However, these methods are also ineffective for mass-production, and have a problem of high production costs.

Moreover, not all enzymes of β-glucosidase, α-L-arabinopyranosidase, α-L-arabinofuranosidase, and α-L-rhamnosidase have the activity of biotransformation of major ginsenosides into minor ginsenosides. For example, the present inventors demonstrated that beta-glucosidase known to be derived from *Arthrobacter chlorophenolicus* A6 has no activity of the biotransformation of ginsenoside. In addition, even though a known enzyme, for example, beta-glucosidase A, has biotransformation activity into Rb1, the activity was not satisfactory.

Further, Korean Patent Application No. 10-1999-0045180 provides a method for preparing ginsenoside Rh2 by degradation of saccharide of PPD-type ginsenoside using saponin alpha-glucosidase. The saponin alpha-glucosidase of the above invention converts ginsenoside Rd into ginsenoside Rh2 via ginsenoside F2. In addition, ginsenoside Rh2 can be produced from ginsenoside Rb1 and Rc. As described in Example 3, however, the saponin alpha-glucosidase should be obtained by removal of bacterial cells from the culture broth of *Aspergillus* in media containing wheat bran and ginseng powder. Thus, the low production yield increases the production cost in mass-production, and loss of the desired product problematically occurs during the production process.

DISCLOSURE

Technical Problem

The present inventors have made many efforts to develop a method for mass-producing minor ginsenosides present in a small amount in plants such as ginseng. As a result, they obtained a ginsenoside glycosidase gene having a biotransformation activity of major ginsenosides into minor ginsenosides from the genus *Terrabacter* strain. The present inventors found that a recombinant enzyme expressed by cloning the gene converts major ginsenosides into minor ginsenosides having high physiological activity and in vivo absorption by selective hydrolysis of a particular molecular bond of major ginsenosides, thereby completing the present invention.

Technical Solution

An object of the present invention is to provide a ginsenoside glycosidase protein derived from the genus *Terrabacter*.

Another object of the present invention is to provide a nucleic acid encoding the protein.

Still another object of the present invention is to provide a recombinant vector comprising the nucleic acid.

Still another object of the present invention is to provide a transformant transformed with the vector.

Still another object of the present invention is to provide a method for preparing ginsenoside glycosidase derived from the genus *Terrabacter*, comprising the steps of culturing the transformant that is transformed with the vector including the gene encoding the ginsenoside glycosidase derived from the genus *Terrabacter*; producing the ginsenoside glycosidase from the cultured transformant; and collecting the produced ginsenoside glycosidase.

Still another object of the present invention is to provide a method for converting PPD-type saponins into soluble saponins using the ginsenoside glycosidase derived from the genus *Terrabacter*.

Still another object of the present invention is to provide a composition for converting PPD-type saponins into in vivo absorbable, soluble saponins comprising the ginsenoside glycosidase derived from the genus *Terrabacter* as an active ingredient.

Advantageous Effects

The genus *Terrabacter*-derived ginsenoside glycosidase of the present invention shows excellent activity of converting ginsenosides into in vivo absorbable forms, and produces a large amount of minor ginsenosides which are only present in nature at a trace amount and thus have limited usage even though their efficacies are demonstrated.

In addition, it can be mass-produced by culturing a transformant that is transformed with a recombinant vector including a gene encoding ginsenoside glycosidase, thereby being industrially applicable.

Figure 9:
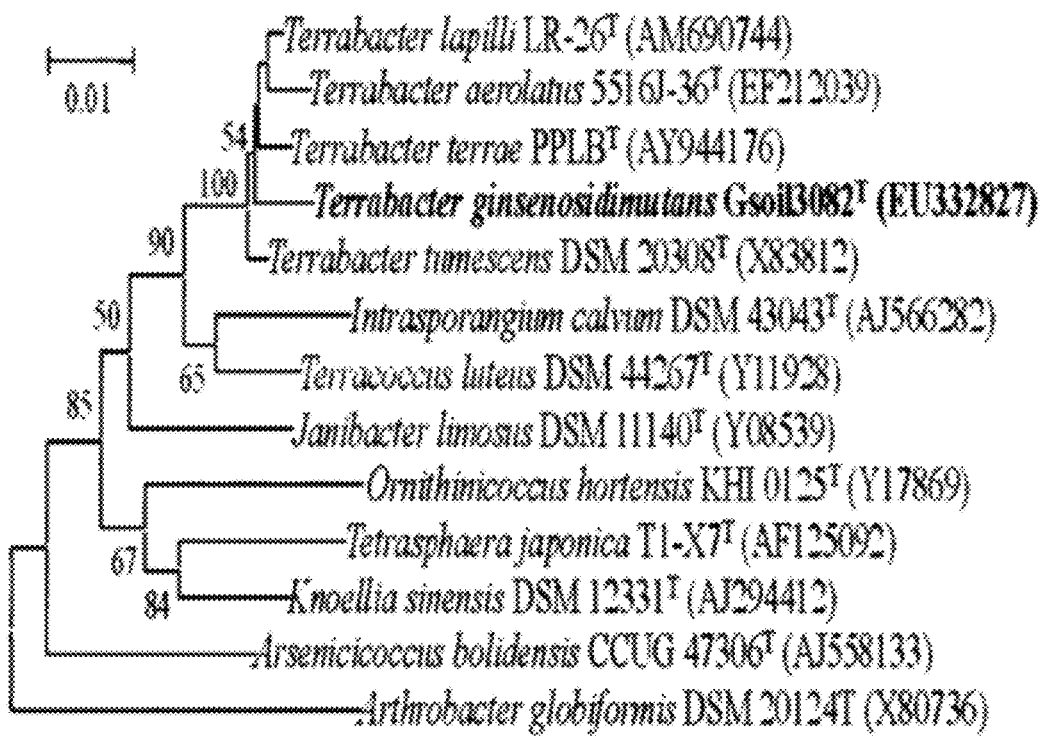
Figure 10:
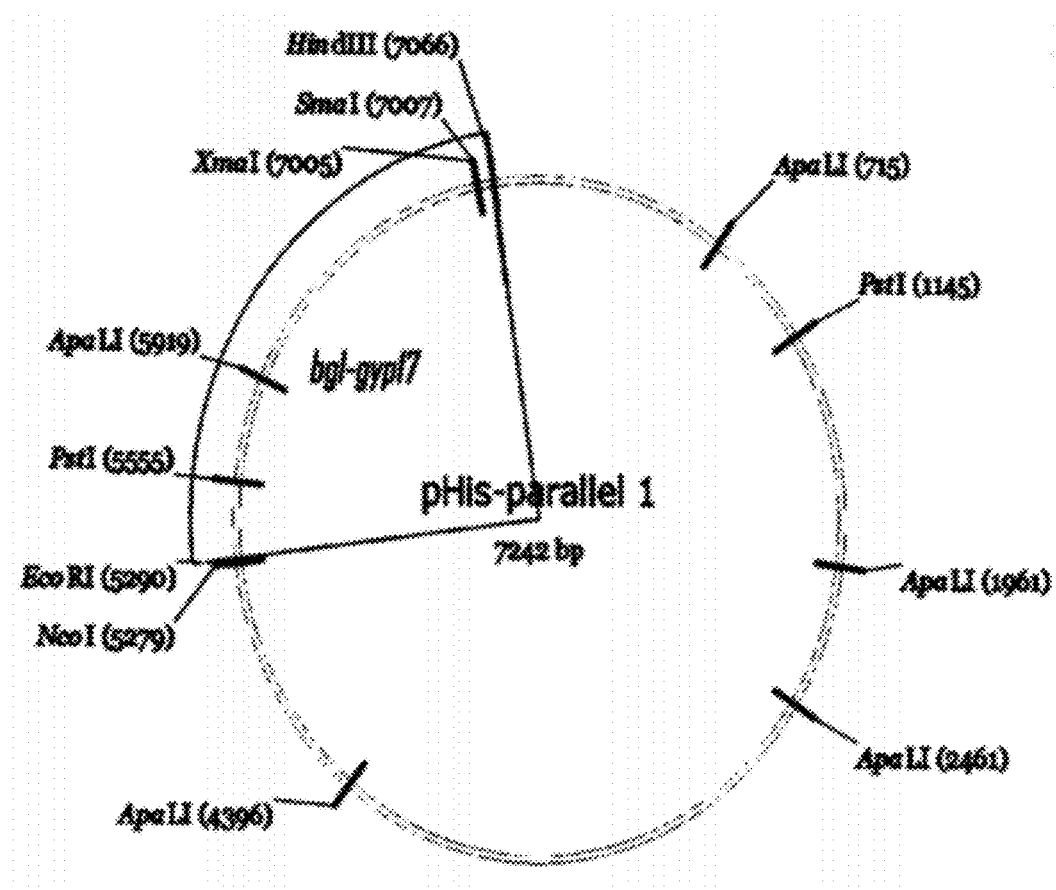

The pH effect on the stability was examined by incubation of the enzyme in 50 mM buffer at 4° C. for 24 hours, and the residual activity was assayed by a standard analysis method. The thermo-dependence of the activity was assayed in 50 mM potassium phosphate buffer at various temperatures ranging from 4 to 90° C. Thermostability was tested by incubating aliquots of the enzyme in 50 mM potassium phosphate buffer for 30 minutes at different temperatures. After cooling the sample on ice for 10 minutes, residual activity was determined by a standard analysis;

FIG. 9 shows a rooted phylogenetic tree based on 16S rRNA sequences of strain Gsoil 3082$^T$ and related Actinobacteria, in which the tree was constructed using the neighbor-joining method (Saitou & Nei, 1987) with a Kimura (1983) two-parameter distance matrix and pairwise deletion, Bootstrap values (expressed as percentages of 1,000 replications) greater than 70% are shown at the branch points, and the bar represents 10 nucleotide substitutions per 1,000 nucleotides; and FIG. 10 shows a plasmid vector including bgl-gyp17.

BEST MODE

In one aspect to achieve the above objects, the present invention provides a ginsenoside glycosidase protein derived from the genus *Terrabacter* (hereinafter, interchangeable with 'ginsenoside glycosidase protein' and 'protein of the present invention').

Glycosidase protein is known to be an enzyme that catalyzes the hydrolysis of the glycosidic linkage of polysaccharides or oligosaccharides such as maltose, sucrose, and turanose. Ginsenoside glycosidase is also known to show different activities in various organisms. There are differences in the activity and function between the enzymes. Preferably, the ginsenoside glycosidase of the present invention is an enzyme derived from the genus *Terrabacter* microorganisms, and converts major ginsenosides into minor forms, which is attributed to its ability of preferentially hydrolyzing glucose at the C-3 position of ginsenoside. Ginsenoside glycosidase has been widely known, but there are no reports on the specific activities and functions of the ginsenoside glycosidase derived from the genus *Terrabacter* microorganisms. In particular, the present inventors first demonstrated that the ginsenoside glycosidase derived from the genus *Terrabacter* is able to convert the ginsenosides Rb1, Rb2 and Rc into minor forms. More preferably, the ginsenoside glycosidase of the present invention can be isolated from Gsoil 3082 which is a putative strain of the genus *Terrabacter*, and this strain was deposited at Korean Collection for Type Cultures (KCTC) of Korea Research Institute of Bioscience and Biotechnology under the Accession number KCTC19421T, and its sequence is represented by SEQ ID NO. 1.

A microorganism for identifying the novel gene of the present invention is the genus *Terrabacter* microorganism, and the novel *Terrabacter* Gsoil 3082 strain first isolated by the present inventors was isolated from a ginseng farm in Pocheon Province, Korea. According to the results of phylogenetic analysis based on the 16S rRNA sequence and phenotype of the strain, the strain was identified as a novel *Terrabacter* strain belonging to the phylum Actinobacteria, and the strain has an ability of converting Rb1 into gypenoside XVII (gyp XVII), and further into gypenoside LXXV (gyp LXXV) and compound K (C—K) when there is a high concentration of the enzyme. In addition, the strain was found to have an ability of converting ginsenoside Rb2 into compound Y, compound O into compound Y, ginsenoside Rc into compound Mc, and compound Mc1 into compound Mc. In order to identify the enzyme having the above activity, the present inventors cloned Bgl-gyp17 by exploring the above novel strain using a fosmid library kit.

The protein of the present invention means an amino acid sequence (polypeptide sequence) constituting the ginsenoside glycosidase derived from the genus *Terrabacter*. Preferably, the *Terrabacter* may be a novel strain Gsoil 3082 that was identified by the present inventors. The amino acid sequence of ginsenoside glycosidase isolated from the strain is a sequence represented by SEQ ID NO. 1. Preferably, in addition to the above sequence, it includes an amino acid sequence having 70% or higher homology, preferably 80% or higher homology, more preferably 90% or higher homology, much more preferably 95% or higher homology, and most preferably 98% or higher homology with the sequence, and includes an amino acid sequence substantially having the ginsenoside glycosidase activity. Further, it is apparent that any type of proteins having a deletion, modification, substitution or addition of some sequence may be within the scope of the present invention, as long as the sequence having the homology is an amino acid sequence having a biological activity that is substantially identical or corresponding to that of the ginsenoside glycosidase.

In another aspect, the present invention provides a nucleic acid encoding the ginsenoside glycosidase derived from the genus *Terrabacter*.

The nucleic acid of the present invention is a nucleic acid encoding the ginsenoside glycosidase derived from the genus *Terrabacter*, and the *Terrabacter* may be preferably isolated from the novel strain Gsoil 3082 that was identified by the present inventors. The ginsenoside glycosidase-encoding nucleic acid sequence isolated from the strain is a nucleic acid sequence represented by SEQ ID NO. 2. Preferably, in addition to the above sequence, it includes a sequence having 70% or higher homology, preferably 80% or higher homology, more preferably 90% or higher homology, much more preferably 95% or higher homology, and most preferably 98% or higher homology with the sequence, and includes a sequence substantially having the ginsenoside glycosidase activity. Preferably, the gene of the present invention was designated as bgl-gyp17 by the present inventors, and the gene includes a nucleic acid of 1770 by in length, and encodes a polypeptide consisting of 589 amino acids.

As used herein, the term "homology" refers to the degree of similarity to the amino acid sequence of a wild type protein, and includes sequences having homology of the above percentage or higher with the sequence encoding the ginsenoside glycosidase of the present invention. Homology comparisons can be conducted by the naked eye or with the aid of readily available sequence comparison programs. A commercially available computer program may express homology between two or more sequences in a percentage, and a homology (%) may be calculated for adjacent sequences.

Those skilled in the art will readily appreciate that artificially modified proteins are also equivalent to the protein as long as they maintain homology greater than a predetermined level and retain the activity of the desirable protein. Therefore, the ginsenoside glycosidase of the present invention includes the amino acid sequence variants of a wild-type, and the term 'variant' means a protein or a nucleic acid in which one or more amino acid residues or nucleic acid sequences differ from the native amino acid sequence or nucleic acid sequence, resulting from a deletion, an insertion, a non-conservative or conservative substitution or combinations thereof.

In still another embodiment, the present invention provides a recombinant vector that includes the nucleic acid encoding the ginsenoside glycosidase derived from the genus *Terrabacter*.

As used herein, the term "vector" is an expression vector for expressing a desired protein in a proper host cell, and refers to a DNA construct including essential regulatory elements operably linked to express a nucleic acid insert. In the present invention, a recombinant vector including the gene encoding ginsenoside glycosidase can preferably be constructed, and a host cell is transformed or transfected with the constructed recombinant vector, thereby obtaining the ginsenoside glycosidase of the present invention. In the preferred Example of the present invention, while fosmid library screening was performed, an ORF encoding ginsenoside glycosidase was identified, and inserted into a pHis-Parallel1 expression vector, thereby preparing a recombinant vector (FIG. 10).

In addition, a host cell such as *E. coli* may be transformed with the recombinant vector constructed by the above method, thereby preparing a transformant. In the preferred Example of the present invention, *E. coli* C41 (DE3) cell was transformed with the recombinant vector to induce expression of ginsenoside glycosidase.

The recombinant vector of the present invention can be obtained by linking (inserting) the gene of the present invention with a proper vector. The vector, into which the gene of the present invention is inserted, is not particularly limited, as long as it is replicable in the host cell. It is exemplified by plasmid DNA, phage DNA or the like. The specific example of plasmid DNA includes commercial plasmids such as pcDNA3.1+ (Invitrogen). Other examples of the plasmid used in the present invention include *E. coli*-derived plasmids (pYG601BR322, pBR325, pUC118 and pUC119), *Bacillus subtilis*-derived plasmids (pUB110 and pTP5), and yeast-derived plasmids (YEp13, YEp24 and YCp50). The specific example of phage DNA includes—phages (Charon4A, Charon21A, EMBL3, EMBL4, gt10, gt11 and ZAP). Further, animal viruses such as retrovirus, adenovirus or vaccinia virus, and insect viruses such as baculovirus may be used. In the preferred Example of the present invention, the recombinant vector was prepared by insertion of the gene of the present invention into the pHis-Parallel1 vector.

Moreover, as the vector of the present invention, a transcriptional activator, such as B42-linked fusion plasmid (e.g., pJG4-5), may be used, and GST, GFP, His-tag, Myc-tag may be applied to the fusion plasmid, but the fusion plasmid of the present invention is not limited to these examples. In the preferred Example of the present invention, in order to facilitate purification and recovery of the expressed ginsenoside glycosidase, a hexahistidine tag (6× his tag, $His_6$ tag) was used.

For insertion of the gene of the present invention into the vector, the purified DNA may be cleaved using proper restriction enzymes, and inserted into the restriction sites or cloning site of a proper vector DNA. The gene of the present invention should be operably linked to the vector. The vector of the present invention may further include cis elements such as an enhancer, a splicing signal, a poly A addition signal, a selection marker, a ribosome binding sequence (SD sequence), in addition to a promoter and the nucleic acid of the present invention. The selection marker may be exemplified by chloramphenicol resistance gene, ampicillin resistance gene, dihydrofolate reductase, neomycin resistance gene or the like, but the operably linked additional elements are not limited to these examples.

In still another embodiment, the present invention provides a transformant that is transformed with the vector including the nucleic acid encoding the ginsenoside glycosidase.

As used herein, the term "transformation" means introduction of DNA into a host cell so that DNA is replicable, either as an extra-chromosomal element or by chromosomal integration, that is, artificial genetic alteration by introducing a foreign DNA into a host cell. The transformation of the present invention may be performed by any transformation method, and is easily performed according to a typical method known in the art. In general, examples of the transformation method include a $CaCl_2$ precipitation, a Hanahan method that is an improved $CaCl_2$ method by using DMSO (dimethyl sulfoxide) as a reducing material, electroporation, calcium phosphate precipitation, protoplast fusion, agitation using silicon carbide fiber, Agrobacterium-mediated transformation, PEG-mediated transformation, dextran sulfate-, lipofectamine-, and desiccation/inhibition-mediated transformation.

The transformation method for the vector including the gene encoding the ginsenoside glycosidase of the present invention is not limited to these examples, and the transformation or transfection methods typically used in the art may be used without limitation.

The transformant of the present invention can be obtained by introducing the recombinant vector including the desired gene encoding ginsenoside glycosidase into a host cell. The host cell is not particularly limited, as long as it is able to express the nucleic acid of the present invention. The specific examples of the host cell to be used in the present invention include bacteria belonging to the genus Escherichia such as E. coli; bacteria belonging to the genus Bacillus such as Bacillus subtilis; bacteria belonging to the genus Pseudomonas such as Pseudomonas putida; yeasts such as Saccharomyces cerevisiae and Schizosaccharomyces pombe; animal cells, and insect cells. The specific examples of E. coli strain to be used in the present invention include CL41(DE3), JM109, and HB101, and the specific examples of Bacillus subtilis strain include WB700 and LKS87. In the preferred Example of the present invention, E. coli CL41(DE3) was used as a host cell to prepare the transformant that is transformed with the vector including ginsenoside glycosidase.

When bacteria such as E. coli are used as host cells, the recombinant vector of the present invention is able to autonomically replicate in the host cells, and consists of a promoter, a ribosome binding sequence, the nucleic acid of the present invention, and a transcription termination sequence. Any promoter can be used as the promoter of the present invention, as long as it is able to drive expression of the gene of the present invention in the host cell such as E. coli. For example, E. coli or phage-derived promoters such as trp promoter, lac promoter, PL promoter, and PR promoter; and E. coli infection phage-derived promoters such as T7 promoter may be used. In addition, artificially modified promoters such as tac promoter may be used.

In order to facilitate the purification of the desired protein to be collected in the present invention, the plasmid vector may further include other sequences, if necessary. The sequences further included may be tag sequences for protein purification, for example, glutathione S-transferase (Pharmacia, USA), maltose binding protein (NEB. USA), FLAG (IBI, USA), and hexahistidine (Quiagen, USA), and is most preferably hexahistidine. However, the type of the sequences needed for the purification of the desired protein is not limited to these examples. In the preferred Example of the present invention, a hexahistidine tag was used to facilitate the purification.

Further, the fusion protein expressed by the vector including the fusion sequence may be purified by affinity chromatography. For example, if glutathione S-transferase is fused, its substrate glutathione can be used. If 6×His tag is used, a Ni-NTA His-bind resin column (Novagen, USA) can be used to facilitate the recovery of the desired protein.

In still another embodiment, the present invention provides a method for preparing the ginsenoside glycosidase derived from the genus Terrabacter. Preferably, the preparation method may include the steps of (a) culturing the transformant that is transformed with the vector including the nucleic acid encoding the ginsenoside glycosidase; (b) producing the ginsenoside glycosidase from the cultured transformant; and (c) collecting the produced ginsenoside glycosidase.

The method of expressing the ginsenoside glycosidase of the present invention is the same as described above, and the host cell transformed with the above method can be cultured by a typical method used in the art. For example, the transformant expressing the ginsenoside glycosidase may be cultured in various media, and fed-batch culture and continuous culture may be performed, but the method of culturing the transformant of the present invention is not limited to these examples. In addition, a carbon source included in the media for growing the host cell may be properly selected by those skilled in the art depending on the type of the prepared transformant, and suitable culture conditions may be adopted to adjust the time and amount of the culture.

When a proper host cell is selected and cultured under the culture conditions, the transformant that is successfully transformed with the desired protein produces ginsenoside glycosidase. The produced ginsenoside glycosidase can be released into the cytoplasm, periplasmic space, or out of the cells according to the vector construction and properties of the host cell. In addition, the desired protein may be expressed in a soluble or insoluble form, but the protein encoded by the bgl-gyp17 gene was expressed in an insoluble form in the Example of the present invention.

The protein expressed inside or outside the host cell may be purified in a typical manner. The purification method is exemplified by salting out (e.g., ammonium sulfate precipitation, sodium phosphate precipitation), solvent precipitation (e.g., protein fractional precipitation using acetone or ethanol), dialysis, gel filtration, chromatography such as ion exchange and reversed phase column chromatography, and ultrafiltration, and these methods may be performed singly or in combination to purify the protein of the present invention.

Absorbable minor ginsenosides can be produced using the ginsenoside glycosidase isolated by the above method in an in vitro or in vivo system containing ginsenoside.

In still another embodiment, the present invention provides a method for converting PPD-type saponins into in-vivo absorbable, soluble saponins using the ginsenoside glycosidase derived from the genus *Terrabacter*, and a composition for converting PPD-type saponins into in vivo absorbable, soluble saponins, including the ginsenoside glycosidase protein derived from the genus *Terrabacter* as an active ingredient.

As the PPD-type saponin used as a starting material in the present invention, isolated and purified saponin, or saponin included in a powder or extract of ginseng or red ginseng may be used. That is, a powder or extract of ginseng or red ginseng comprising saponin may be directly used as a starting material to perform the method of the present invention. The ginseng used in the present invention includes the known various types of ginsengs, such as *Panax ginseng*, *Panay quiquefolius* (*P. quiquefolius*), *Panay notoginseng* (*P. notoginseng*), *Panax japonicus* (*P. japonicus*), *Panay trifolium* (*P. trifolium*), *Panax pseudoginseng* (*P. pseudoginseng*) and *Panay vietnamensis* (*P. vietnamensis*), but is not limited thereto.

As mentioned in description of the related art, saponins are classified into three groups based on their aglycone structure: Protopanaxadiol-type ginsenosides, Protopanaxatriol-type ginsenosides, and Oleanolic acid-type ginsenosides. The PPD-type saponins of the present invention mean Protopanaxadiol-type ginsenosides. The genus *Terrabacter*-derived ginsenoside glycosidase of the present invention is used to convert them into "soluble saponins", which means that the unabsorbable major ginsenosides (e.g., Rb1, Rb2, Rc, Rg1 and Re) can be converted into the relatively absorbable minor ginsenosides (F2, Rg3 and Rh1), compound O, compound Y, compound Mc1, compound Mc, compound K, gypenoside XVII or gypenoside LXXV by subsequent hydrolysis at the C-3 position of ginsenosides.

Preferably, the conversion may occur through bioconversion, and it may be achieved by continuous or discontinuous, selective hydrolysis at the C-3 position of ginsenosides. The protein of the present invention is able to convert all of the PPD-type ginsenosides known in the art into the absorbable minor forms, and the preferred examples of the bioconversion by the protein of the present invention include conversion of ginsenoside Rb1 into gypenoside XVII, conversion of gypenoside XVII into gypenoside LXXV, conversion of gypenoside LXXV into compound-K, conversion of ginsenoside Rb2 into compound Y, conversion of compound O into compound Y, conversion of ginsenoside Rc into compound Mc, and conversion of compound Mc1 into compound Mc. Additionally, these conversions may include conversion of the starting material, ginsenoside Rd into compound K, conversion of the starting material, ginsenoside F2 into compound K, conversion of the starting material, ginsenoside Rg3 into PPD, and conversion of the starting material, ginsenoside Rh2 into PPD.

More particularly, when the composition including the protein of the present invention was added to ginsenoside Rb1, compound K was produced, and gypenoside XVII and gypenoside LXXV were produced as intermediate materials. In addition, when the protein of the present invention was added to ginsenoside Rd as a starting material, compound K was produced, and F2 was produced as an intermediate material. When the protein of the present invention was added to Rg3 as a starting material, PPD was produced, and ginsenoside Rh2 was produced as an intermediate material. When Rb2 was used as a starting material, the protein of the present invention produced compound Y (Notoginsenoside) via compound O (Notoginsenoside L). When ginsenoside Rc was used as a starting material, the protein of the present invention produced compound Mc (Notoginsenoside) via compound Mc1 (Notoginsenoside L). These procedures may be performed by hydrolysis at the C-3 position of ginsenosides using the protein of the present invention, and the products (ginsenoside derivatives) produced by the hydrolysis are more absorbable than the reactants.

In addition, these bioconversions can adjust the amount of the final products in a reactant or enzyme concentration-dependent manner. Preferably, if the enzyme concentration is 0.01 mg/ml, most Rb1 is converted into gyp XVII, and if the enzyme concentration is 0.1 mg/ml, it can be further converted into gyp LXXV, and if the enzyme concentration is 1 mg/ml, it can be further converted into compound K.

MODE FOR INVENTION

Hereinafter, the present invention will be described in more detail with reference to Examples. However, these Examples are for illustrative purposes only, and the invention is not intended to be limited thereby.

Example 1

Taxonomic Characterization of Novel Strain Gsoil 3082

Gsoil 3082 was cultured on R2A at 30° C. After culturing for 3 days, cell morphology was observed under a Nikon light microscope. Typical physiological and biochemical characterization assays, including Gram staining, anaerobic growth, and catalase activity, were carried out as described in Bergey's Manual of Systematic Bacteriology. The assimilation of substrates as the sole carbon source and enzymatic activities were determined using the API 20 NE, API ID 32 GN, and API ZYM test kits (bioMerieux). Growth at different temperatures (4, 15, 20, 25, 30, 37, 42, and 45° C.) and various pH levels (pH 4.5 to 10.0 at intervals of 0.5 pH unit) was assessed after a 5-day incubation period.

Growth on nutrient agar and TSA (trypticase soy agar) was also evaluated at 30° C. Chemotaxonomic analysis was performed according to the method of Montero-Barrientos et al.

The phylogenetic relatedness of strain Gsoil 3082 to other bacteria was determined by analyzing a portion of the 16S rRNA gene. PCR amplification was amplified by PCR using the universal primers, 27F (5'-AGAGTTTGATCMTGGCT-CAG-3') (SEQ ID NO. 3) and 1492R (5'-TACGGYTACCT-TGTTACGACTT-3') (SEQ ID NO. 4) and then sequenced (SolGent, Daejeon, Korea). A near-complete sequence of the 16S rRNA gene was compiled using the SeqMan program (DNASTAR), and a blast search was performed on the NCBI database (Accession number: EU332827). Sequences of the 16S rRNA genes of related taxa were obtained from the GenBank database. Phylogenetic distances of the strain were determined by phylogenetic tree based on the sequences using the Kimura two-parameter model. A phylogenetic tree was constructed by the neighbor-joining method using the MEGA3 program with bootstrap values based on 1,000 replicates. DNA-DNA hybridization analysis was performed fluorometrically according to the method of Ezaki et al. using photobiotin-labeled DNA probes and microdilution wells. The highest and lowest values obtained for each sample were excluded, and the means of the remaining values were reported as the relatedness value.

Characterization of Gsoil 3082

After four rounds of screening, 20 novel bacterial strains (Rhodanobacter ref. 60) converting major ginsenosides into minor ginsenosides were isolated from the soil of a ginseng farm in Pocheon Province, Korea. One of the isolates was designated as Gsoil 3082, and it was first demonstrated that this strain is able to hydrolyze ginsenoside Rb1 into gyp XVII and gyp LXXV. The HPLC and NMR results of bioconversion pathway of ginsenoside Rb1 showed that Gsoil 3082 strain is able to convert ginsenoside Rb1 into gyp XVII and gyp LXXV by hydrolysis of the outer and inner glucose at C-3 position of ginsenoside Rb1. In addition, the Gsoil 3082 strain was characterized by a polyphasic approach to clarify its taxonomic position and used to clone a ginsenoside glycosidase gene.

The isolated strain was Gram positive, aerobic, nonmotile, non-spore forming, and short rod shaped. Phylogenetic analysis based on 16S RNA gene sequences indicated that the isolate belongs to the genus *Terrabacter* in the phylum Actinobacteria, and is most closely related to *T. tumescens* DSM20308$^T$ (98.4 similarity), followed by *T. terrae* PPLB$^T$ (98.2), and *T. aerolatum* 5516J-36$^T$ (98.0) (see FIG. 9). The G+C content of the genomic DNA was 68.2 mol %. Chemotaxonomic data [major menaquinone—MK-8(H4), main polar lipids (phosphatidylethanolamine, diphosphatidylglycerol and phosphatidylinositol) and major fatty acid—iso-$C_{15:0}$, anteiso-$C_{15:0}$ and iso-$C_{16:0}$] support that Gsoil 3082 belongs to the genus *Terrabacter* (Table 1). DNA-DNA relatedness values between strains Gsoil 3082$^T$, and *T. tumescens* DSM20308$^T$, *T. terrae* PPLB$^T$ and *T. aerolatum* 5516J-36$^T$ were 43, 34 and 31, respectively, suggesting that Gsoil 3082 should be classified as a novel species (Wayne et al., 1987).

Moreover, physiological and biochemical tests showed that there is a morphological difference between the isolate and other strains of the genus *Terrabacter* (Table 2). Therefore, the genus *Terrabacter* Gsoil 3082 first isolated by the present inventors was deposited at the Korean Collection for Type Cultures (KCTC) under the Accession number KCTC19421T, and designated as *Terrabacter ginsenosidimutans* sp.

TABLE 1

Fatty acid profiles of Gsoil 3082$^T$ strain and other related strains

| Fatty acid | 1 | 2 | 3 | 4 | 5 |
| --- | --- | --- | --- | --- | --- |
| Saturated | | | | | |
| $C_{12:0}$ | — | — | 1.2 | — | — |
| $C_{14:0}$ | — | 5.8 | — | 1.8 | — |
| $C_{15:0}$ | — | — | 1.0 | — | — |
| $C_{16:0}$ | 8.0 | 11.5 | 2.4 | 5.6 | 3.3 |
| $C_{17:0}$ | 1.4 | 5.5 | 1.2 | 1.6 | 1.4 |
| $C_{18:0}$ | 2.6 | 5.4 | 3.3 | 2.3 | 3.2 |
| Unsaturated | | | | | |
| $C_{17:1}\,\omega 8c$ | 2.1 | 7.3 | 4.7 | 2.4 | — |
| $C_{18:1}\,\omega 9c$ | — | 13.1 | 1.2 | 4.3 | — |
| Branched-chain fatty acid | | | | | |
| iso-$C_{14:0}$ | 6.7 | 5.5 | 3.9 | 3.1 | 7.9 |
| iso-$C_{15:0}$ | 37.6 | 49.0 | 43.0 | 17.2 | 32.0 |
| anteiso-$C_{15:0}$ | 6.9 | 6.5 | 3.0 | 19.6 | 5.2 |
| iso-$C_{16:0}$ | 9.3 | 6.1 | 8.3 | 5.2 | 14.5 |
| iso-$C_{16:1}$ H | 2.3 | — | 5.1 | — | — |
| iso-$C_{17:0}$ | 2.6 | — | — | 2.0 | 5.8 |
| anteiso-$C_{17:0}$ | — | 2.0 | — | 7.2 | 3.1 |
| iso-$C_{17:1}\,\omega 9c$ | 2.3 | — | 3.9 | 1.6 | — |
| anteiso-$C_{17:1}\,\omega 9c$ | — | — | — | 2.3 | — |
| anteiso-$C_{17:0}$ | 2.6 | — | — | — | — |
| Hydroxy fatty fatty acid | | | | | |
| $C_{16:1}$ 2-OH | — | — | 1.3 | — | — |
| $C_{17:0}$ 3-OH | — | — | 1.3 | — | — |
| Methyl ester | | | | | |
| $C_{16:0}$ 10 methyl | — | 1.6 | — | — | — |
| $C_{17:0}$ 10 methyl | — | — | 6.3 | — | — |
| Summed feature 2 | — | — | 2.0 | — | — |
| Summed feature 3 | 1.2 | 7.1 | — | 7.1 | 1.0 |

Summed feature 2 comprises any combination of iso-$C_{15:0}$ I and/or $C_{13:0}$ 3-OH.
Summed feature 3 comprises any combination of iso-$C_{15:0}$ 2OH and/or $C_{16:1}\,\omega 7c$.
Strains: 1, *Terrabacter ginsenosidimutans* Gsoil 3082$^T$; 2, *T. tumescens* DSM 20308$^T$; 3, *T. lapilli* LR-26$^T$; 4, *T. terrae* PPLB$^T$; 5, *T. aerolatus* 5516J-36$^T$.
Data in column 3 is from Lee et al. (2008) and data in columns 2, 4 and 5 are from Weon et al. (2008).
Fatty acids that account for <1.0% of the total are not shown.

TABLE 2

Biochemical characteristics of Gsoil 3082$^T$ strain and other related strains

| Characteristic | 1 | 2 | 3 | 4 | 5 |
| --- | --- | --- | --- | --- | --- |
| Growth at/on: | | | | | |
| pH 4.1 | − | − | + | − | + |
| pH 12.1 | − | + | w | − | − |
| 10° C. | + | + | + | − | + |
| 40° C. | + | − | + | −(+) | − |
| 5% NaCl | + | + | − | −(+) | + |
| Nitrate reduction | + | + | + | − | + |
| Gelatin hydrolysis | w | + | + | − | + |
| Enzyme activities (API ZYM) | | | | | |
| Esterase (C4) | + | − | − | − | + |
| Lipase (C14) | − | − | − | −(+) | + |
| Valine arylamidase | − | − | + | − | − |
| Cystine arylamidase | − | − | + | − | − |
| Naphthol-AS-BI-phosphohydrolase | + | − | − | −(+) | + |
| Acid phosphatase | + | + | + | − | + |
| G + C content (mol %) | 69.2 | 69.2-72.4 | 72.6 | 71.0 | 71.7 |

Strains: 1, *Terrabacter ginsenosidimutans* Gsoil 3082$^T$; 2, *T. tumescens* DSM 20308$^T$; 3, *T. lapilli* LR-26$^T$; 4, *T. terrae* PPLB$^T$; 5, *T. aerolatus* 5516J-36$^T$.
Data in columns 2-4 are from Lee et al. (2008) and data in column 5 is from Weon et al. (2008).
+, Positive; −, negative; W, weak reaction; V, variable among studies; ND, no data available.

Structural Identification of Metabolites

Metabolite (1) was obtained as a white powder and displayed a molecular ion peak [M+H]$^+$ at m/z 947.5581 in HR-ESIMS, corresponding to the elemental formula $C_{48}H_{83}O_{18}$ (molecular weight, 947.5579). As shown in Table 3, the $^1$H- and $^{13}$C-NMR spectroscopic data of metabolite (1) closely resembled Gyp XVII previously published. Heteronuclear multiple bond correlations spectrum (HMBC) spectrum of δH 5.14 (1H, d, J=7.2 Hz, H-1") to δC 83.9 (C-20) and δH 4.95 (1H, d, J=7.2 Hz, H-1') to δC 89.3 (C-3) enabled the assignment of a glucose residue to both C-20 and C-3. The remaining glucose was affixed to C-6", as determined by the long-range correlation between δH 5.11 (1H, d, J=7.2 Hz, H-1"') and δC 70.7 (C-6") in the HMBC spectrum. Thus, metabolite (1) was confirmed as Gyp XVII.

Metabolite (2) displayed a molecular ion peak $[M+H]^+$ at m/z 785.5089 in HR-ESIMS, corresponding to the elemental formula $C_{42}H_{73}O_{13}$ (molecular weight, 785.5051). As shown in Table 3, the $^1H$- and $^{13}C$-NMR spectroscopic data of metabolite (2) were similar to those of metabolite (1), but lacked the proton and carbon signals of 1 glucose unit. Only two anomeric proton signals were observed at δH 5.09 (1H, d, J=7.8 Hz, H-1") and 5.06 (1H, d, J=7.6 Hz, H-1'), and the corresponding carbon signals were detected at δC 98.3 (C-1") and 105.5 (C-1') in the $^1H$- and $^{13}C$-NMR spectra, respectively, implying the presence of two glucose residues in metabolite (2). In the $^{13}C$-NMR spectrum, the chemical shift of C-3 (δC 78.5) of metabolite (2) appeared more pronounced than that of metabolite (1) (δC 89.3), suggesting that there was a free hydroxyl group at C-3 in metabolite (2). Accordingly, the structure of metabolite (2) was established as Gyp LXXV.

TABLE 3

$^1H$- and $^{13}C$-NMR Data of ginsenoside Rb1 metabolite 1 and 2.

| Position | Metabolite 1 | | Metabolite 2 | |
|---|---|---|---|---|
| | δ(C) | δ(H) | δ(C) | δ(H) |
| CH$_2$(1) | 39.7 | | 39.7 | |
| CH$_2$(2) | 27.1 | | 26.0 | |
| H—C (3) | 89.3 | 3.38(dd, J = 10.4, 4.0) | 78.5 | 3.41(dd, J = 10.1, 6.0) |
| C(4) | 40.2 | | 39.8 | |
| H—C (5) | 56.9 | | 56.7 | |
| CH$_2$(6) | 18.9 | | 19.0 | |
| CH$_2$(7) | 35.6 | | 35.3 | |
| C(8) | 40.5 | | 40.4 | |
| H—C(9) | 50.7 | | 50.6 | |
| H—C (10) | 37.4 | | 36.7 | |
| CH$_2$(11) | 31.3 | | 31.1 | |
| H—C (12) | 70.7 | 4.22(m) | 70.6 | 4.20(m) |
| H—C (13) | 50.0 | | 49.7 | |
| C(14) | 51.9 | | 51.7 | |
| CH$_2$(15) | 31.2 | | 29.0 | |
| CH$_2$(16) | 27.3 | | 26.9 | |
| H—C (17) | 52.1 | | 52.0 | |
| Me (18) | 16.5 | 0.97(s) | 16.3 | 0.93(s) |
| Me (19) | 16.8 | 0.82(s) | 16.5 | 0.85(s) |
| C(20) | 83.9 | | 83.9 | |
| Me (21) | 22.9 | 1.67(s) | 22.7 | 1.65(s) |
| CH$_2$(22) | 36.7 | | 36.5 | |
| CH$_2$(23) | 23.7 | | 23.5 | |
| H—C (24) | 126.5 | 5.33(brt, J = 4.0) | 126.2 | 5.36(overlapped with H2O peak) |
| C(25) | 131.5 | | 131.4 | |
| Me (26) | 26.3 | 1.61(s) | 26.0 | 1.59(s) |
| Me (27) | 18.5 | 1.67(s) | 18.2 | 1.62(s) |
| Me (28) | 28.6 | 1.32(s) | 28.4 | 1.20(s) |
| Me (29) | 17.3 | 1.00(s) | 16.6 | 1.00(s) |
| Me (30) | 17.9 | 0.99(s) | 17.7 | 0.96 (s) |
| H—C (1') | 107.5 | 4.95 (d, J = 7.2) | 105.5 | 5.06 (d, J = 7.6) |
| H—C (2') | 76.3 | | 75.4 | |
| H—C (3') | 79.3 | | 78.5 | |
| H—C (4') | 72.4 | | 72.0 | |
| H—C (5') | 78.9 | | 78.5 | |
| CH$_2$(6') | 63.6 | | 63.1 | |
| H—C (1") | 98.6 | 5.14 (d, J = 7.2) | 98.3 | 5.09 (d, J = 7.8) |
| H—C (2") | 75.4 | | 75.2 | |
| H—C (3") | 79.8 | | 79.3 | |
| H—C (4") | 72.1 | | 71.8 | |
| H—C (5") | 77.6 | | 77.1 | |
| CH$_2$(6") | 70.6 | | 70.5 | |
| H—C (1''') | 105.9 | 5.11 (d, J = 7.2) | | |
| H—C (2''') | 75.8 | | | |
| H—C (3''') | 78.9 | | | |
| H—C (4''') | 72.2 | | | |
| CH$_2$(5''') | 78.8 | | | |
| CH$_2$(6''') | 63.3 | | | |

Example 2

Fosmid Library Screening and Sequencing

A CopyControl Fosmid Library Production Kit (Epicentre, U.S.A) was used according to the manufacturer's instructions. The genomic DNA of the genus *Terrabacter* Gsoil 3082 was randomly cleaved to a fragment of approximately 40 Kb. A small amount thereof was run by Pulsed Field Gel Electrophoresis to determine the size of the cleaved DNA. The blunt, 5'-phosphorylated end was prepared by end-repair. The end-repaired DNA of 40 Kb or longer was selected by LMP (low melting point) agarose gel electrophoresis. The blunt end DNA was purified from the LMP agarose gel, and ligated into a pCC1FOS vector. A MaxPlax lambda packaging extract kit (Epicentre, U.S.A.) was used to perform in vitro packaging. Finally, the product was transfected into *E. coli* EPI300-T1$^R$ that was cultured in LB broth containing 10 mM MgSO$_4$ until the OD value at 600 nm reached 0.6. Absorption of the transfected bacteria was allowed at 37° C. for 20 minutes, and the bacteria were spread on an LB plate containing 12.5 μg/ml chloramphenicol and 27μ-X-gal(5-Bromo-4-chloro-3-indolyl-beta-D-glucoside) and cultured at 37° C. After 16-20 hours, blue colonies (putative ginsenoside glycosidase-producing clones) were selected, and the activity was further examined on the same plate. Then, the putative clones were cultured in 0.2 ml of LB broth containing 12.5 μg/ml chloramphenicol at 37° C. for 24 hours. For analysis of ginsenoside-hydrolytic ability, TLC analysis was used.

The fosmid DNA converting ginsenoside Rb1 into gypX-VII, which was a putative pbgl-gin18 fosmid clone, was identified from the cell culture, and purified using a FosmidMAX DNA purification kit (Epicentre) according to the manufacturer's instructions. The purified fosmid DNA was analyzed by full sequencing. Transposon insertion was performed using a HyperMu <KAN-1> Insertion Kit (Epicentre. U.S.A) according to the manufacturer's protocol. Sequencing of selective insertion clones was performed using two primers of MUKAN-1 FP-1 [5'-CTGGTCCACCTACAACAAAGG-3'] (SEQ ID NO. 5) and RP-1 [5'-AGAGATTTTGAGACAG-GATCCG-3'] (SEQ ID NO. 6) in both directions, thereby obtaining a full sequence, which contains the terminal similarity region of HyperMu transposon inserted in the kit. An ABI PRISM™ Bigdye™ Cycle Sequencing Ready Reaction Kit was used as a template to perform DNA base sequencing reaction. Data collection and analysis were performed using an ABI 3730XL caillary DNA sequencer.

Example 3

Molecular Cloning, Expression, and Purification of Recombinant BGL-GYP17

(3-1) Molecular Cloning and Expression of Recombinant BGL-GYP17

The assembled DNA sequence of pbgl-gin18 was analyzed using a genetic code I and National Center for Biotechnology Information's ORF FINDER. BLASTP was used to identify ORF encoding a putative ginsenoside glycosidase. The template pbgl-gin18 DNA was amplified by PCR using the following oligonucleotide primers.

```
Forward primer:
                                    (SEQ ID NO. 7)
5'-CG GAA TTC ATG GAT CCC TAC GAG GAC CCC-3'

Reverse primer:
                                    (SEQ ID NO. 8)
5'-CCC AAGC TT ACC CCG GGA CGA CGA GGC-3'
```

(in the primer sequences, EcoRI and HindIII restriction sites are underlined)

The amplified fragment was sequentially cloned into a pHis-Parallel expression vector (used by introduction of EcoRI and HindIII restriction sites) and a recombinant TEV protease (rTEV)-containing $His_6$ (hexahistidine) fusion protein expression vector. Next, the recombinant vector pHis-Parallel1 was introduced into *E. coli* C41(DE3).

(3-2) Results of Cloning and Expression of bgl-gyp17

The recombinant ginsenoside glycosidase showed the ability of converting ginsenoside Rb1 into gyp XVII, and thus the present inventors designed the ORF with bgl-gyp17. The putative amino acid sequence of bgl-gyp17 had 589 residues and a molecular weight of 68 kDa.

(3-3) Purification of Recombinant BGL-GYP17

*E. coli* C41(DE3) containing an overexpressing plasmid was cultured in LB-ampicillin media at 37° C. when the OD value at 600 nm reached 0.6, and treated with 0.5 mM isopropyl-β-D-thiogalactopyranoside for 12 hours to induce protein expression. The bacterial cells were obtained by centrifugation at 4° C. and 5,000×g for 20 minutes. The cell pellet was resuspended in a solution (suspension) consisting of 50 mM sodium phosphate, 5 mM EDTA, and 1% Triton X-100 (pH 7.0) and subjected to ultrasonification. Since the recombinant ginsenoside glycosidase was expressed as an insoluble inclusion body, the sonicated lysate was centrifuged at 4° C. and 20,000×g for 30 minutes to obtain a pellet. The pellet was washed twice with a suspension solution in the absence of Triton X-100. The inclusion body was stirred in a solution containing 50 mM sodium phosphate, 5 mM EDTA, and 8 M urea (pH 8.0) at room temperature overnight for solubilization. After centrifugation (20,000×g, 30 minutes, 4° C.), the solubilized protein was diluted with 40 volumes of a refolding buffer containing 50 mM sodium phosphate, 5% glycerol, 0.05% polyethylene glycol and 0.5 mM sodium chloride at pH 7.0, and refolding of the protein was performed at 4° C. for 24 hours. The refolded recombinant ginsenoside glycosidase was reacted with 1 mg/ml Rb1 solution in 50 mM sodium phosphate, followed by TLC analysis. As a result, ginsenoside glycosidase converted ginsenoside Rb1 into gyp XVII. Since the ginsenoside glycosidase-encoding gene was designed with bgl-gyp17, the refolded recombinant bgl-gyp17 was loaded on a Nickel-charged HisTrap column (HisTrap HP, 5 ml bed volume, Gel health), and pre-equilibrated with buffer A (50 mM sodium phosphate, pH 7.0) at 4° C. The resin was washed with buffer A, and the binding protein was eluted with buffer A containing 200 mM imidazole. $His_6$-tag was separated from the protein by culturing rTEV using the HisTrap column, and additional purification was performed on the column containing 30 ml DEAE-cellulose DE-52 (Whatman) using 50 mM sodium phosphate at pH 7.0 and 300 mM NaCl. After purification, 7-residue cloning artifact (GAMDPEF) was contained in the N-terminus of the protein. Protein similarity was determined by 10% SDS-PAGE and Coomassie Blue staining. Dialysis of the purified protein was performed at a concentration of 10 mg/ml using an Amicon Ultra-15 filter (Millipore, U.S.A) and 50 mM sodium phosphate at pH 7.0, and stored at −80° C. until use.

Enzyme analysis and kinetic analysis were performed using the $His_6$-tagged protein purified in 50 mM sodium phosphate at pH 7.0. Gel-filtration analysis was performed on a Sepharose 6 10/300GL (GE Healthcare) column. Measurement was performed using the Bio-Rad filtration standard (catalog no. 151-1901) (Table 4).

TABLE 4

Enzyme purification scheme of Bgl-gyp17

| Purification steps | Volume (ml) | Protein concentration (mg/ml) | Total protein (mg) | Specific activity (U/mg) | Total activity (U*) | Purification (Fold) | Yeild (%) |
|---|---|---|---|---|---|---|---|
| Crude extract | 30 | 7.27 | 218.1 | 23.4 | 5101 | 1.00 | 100.0 |
| Ni purification | 200 | 0.27 | 54.0 | 65.0 | 3511 | 2.78 | 68.8 |
| DEAE-cellulose purification | 144 | 0.05 | 7.2 | 65.8 | 474 | 2.81 | 9.3 |

*One unit(U) of β-p-glucosidase was defined as the amount of enzyme liberating 1 μmol/min of p-nitrophenyl.

(3-4) Purification Result of Recombinant BGL-GYP17

Figure 1:
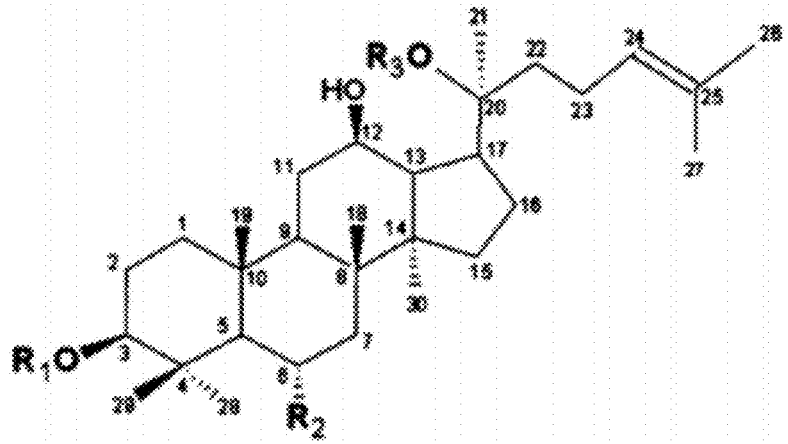
FIG. 1 shows a variety of PPD- and PPT-type ginsenosides.
Figure 2:
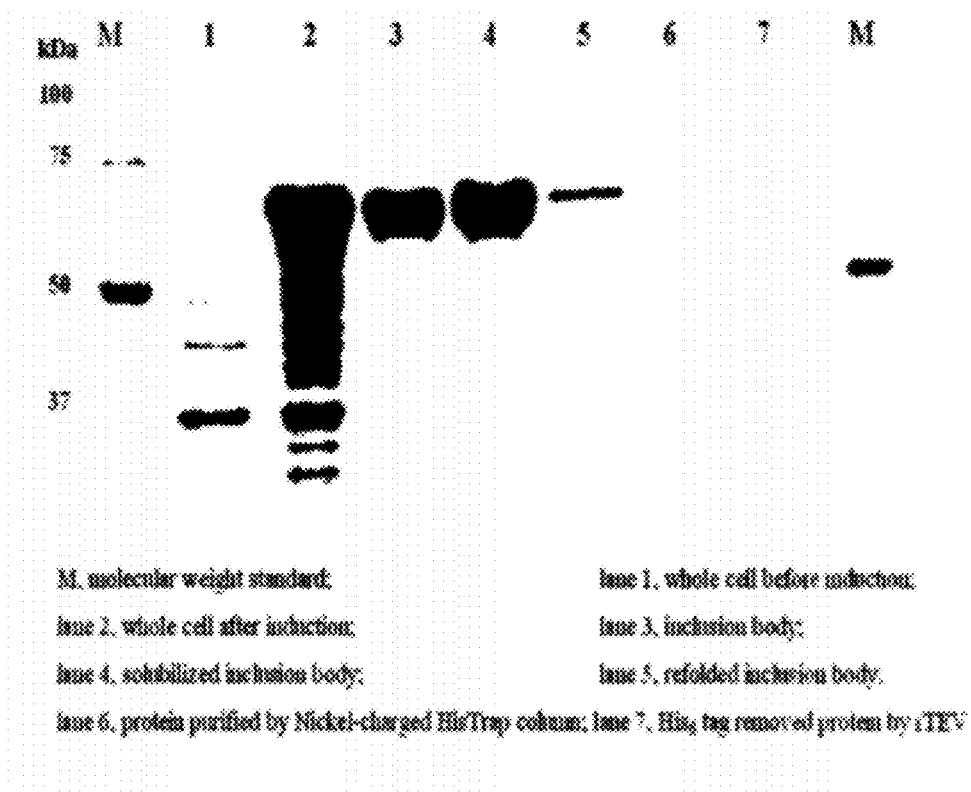
FIG. 2 shows the results of SDS-PAGE for purification of the enzyme, Bgl-gyp17 (M, sample lane (molecular mass standard); lane 1, Crude cell before induction; lane 2, Crude cell after induction; lane 3, inclusion body; lane 4, solubilized inclusion body; lane 5, refolded inclusion body; lane 6, Protein purified by Nickel-charged His Trap column; and lane 7, $His_6$ tag-removed protein by rTEV, the recombinant tobacco etch virus protease.
Figure 3:
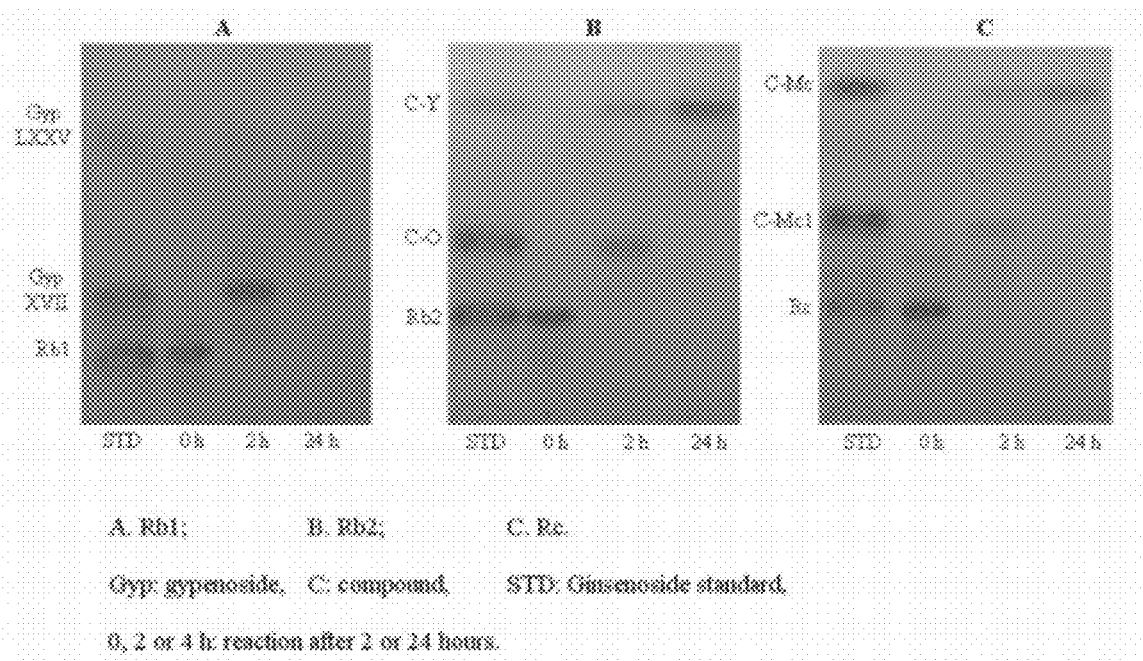
FIG. 3 is TLC result showing bioconversion of major ginsenosides Rb1, Rb2 and Rc by Bgl-gyp17.
Figure 4:
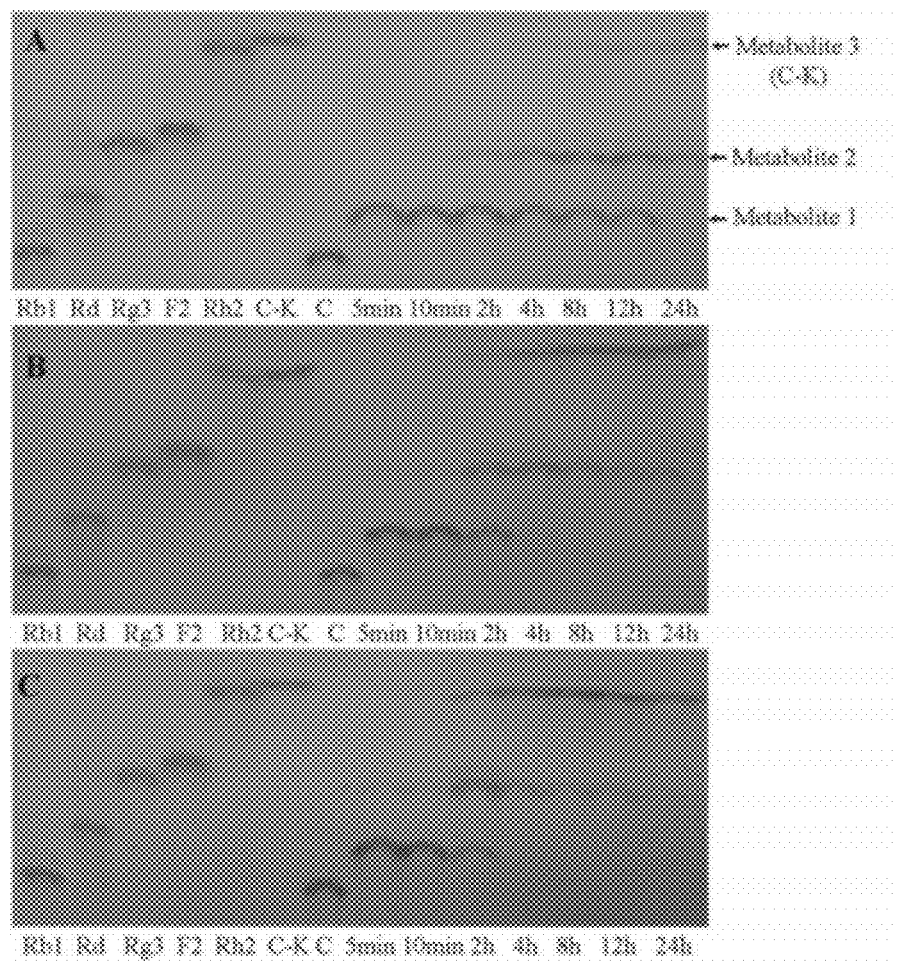
FIG. 4 Analysis of the time course ginsenoside Rb1 bioconversion by BgpA using TLC at enzyme concentrations of 0.1 mg/ml (A), 0.5 mgl/ml (B) and 1.0 mg/ml (C). Lane: Rb1 to C—K, Standard; 0 to 24 h, reaction time.
Figure 5:
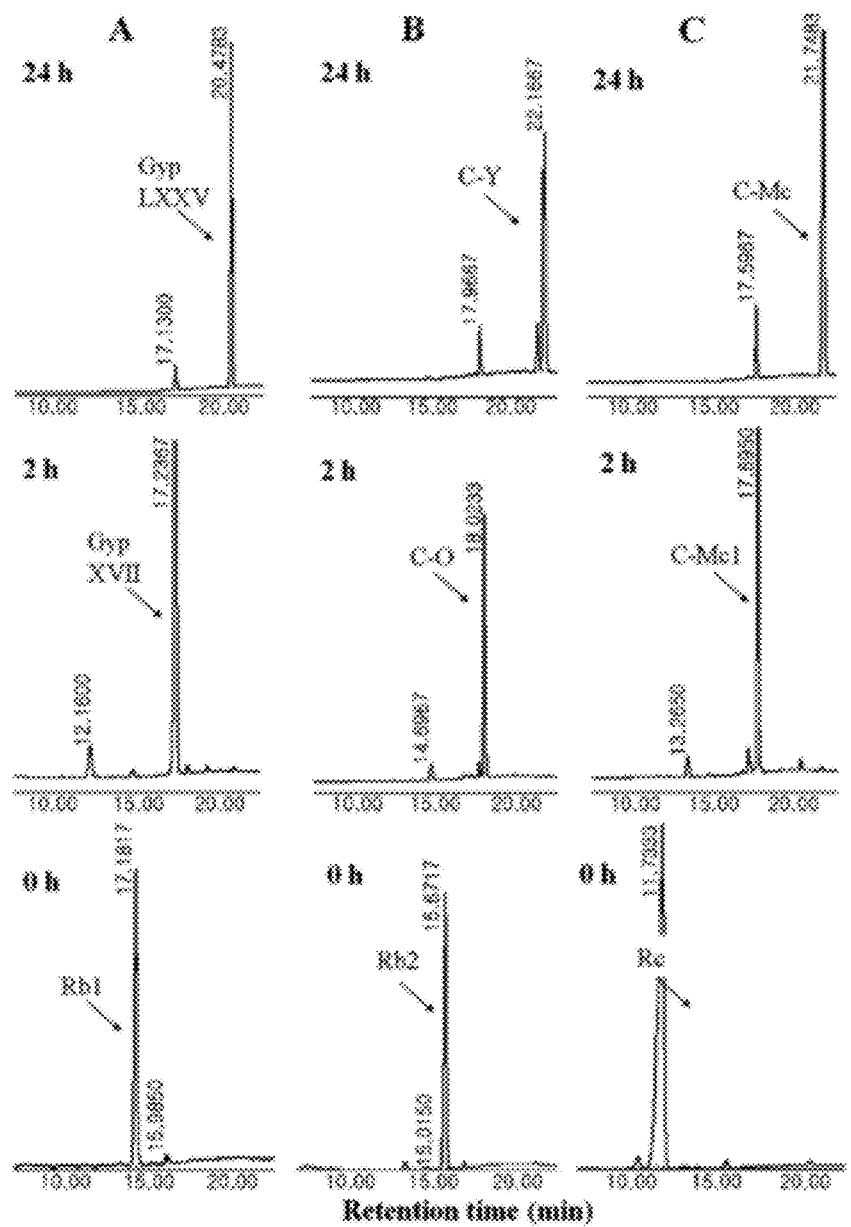
FIG. 5 is HPLC result showing time course of the bioconversion of major ginsenosides Rb1, Rb2 and Rc by Bgl-gyp17.
Figure 6:
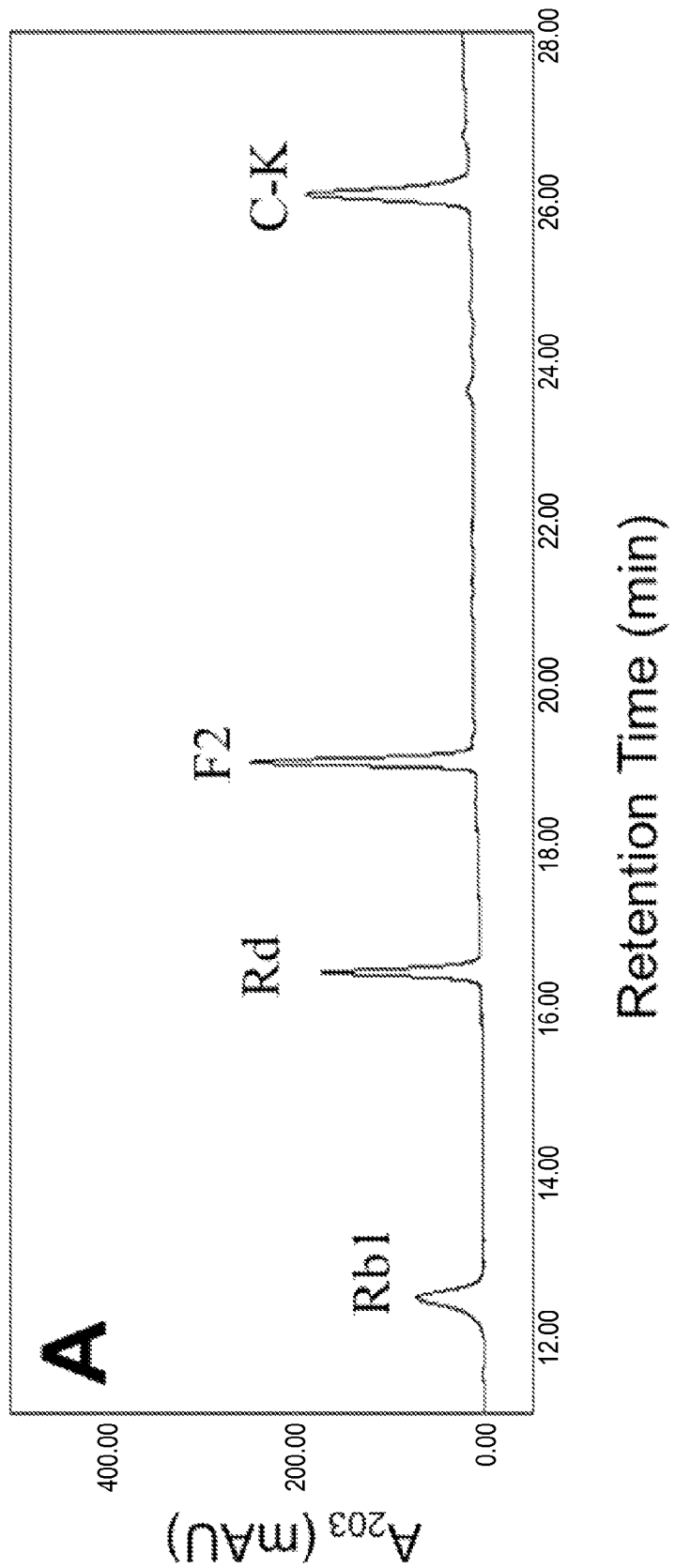
FIG. 6 HPLC analysis of hydrolysis products by BgpA. A. Standard compounds; B. Substrate Rb1; C. after 5 min at the enzyme concentration of 0.1 mg/ml; D. after 4 h at the enzyme concentration of 0.5 mg/ml; E. after 24 h at the enzyme concentration of 1.0 mg/ml.
Figure 6:
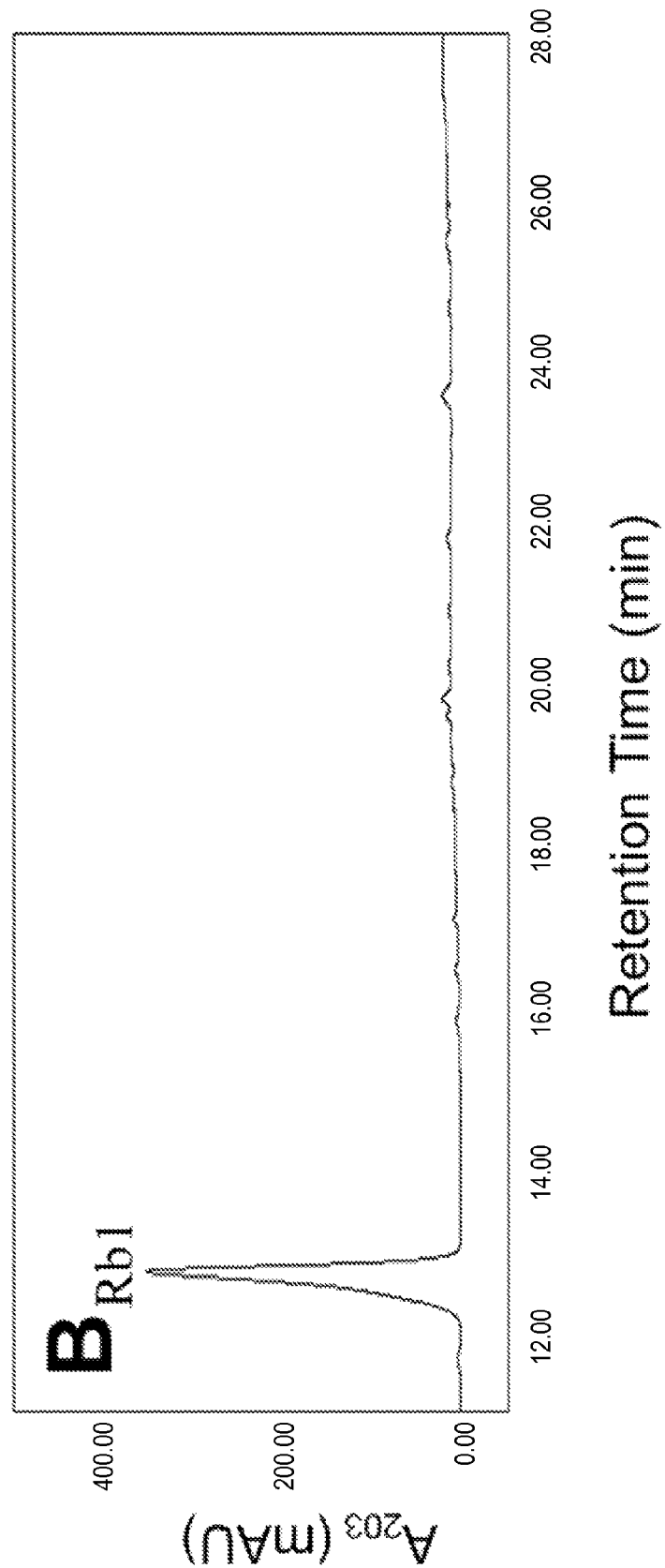
Figure 6:
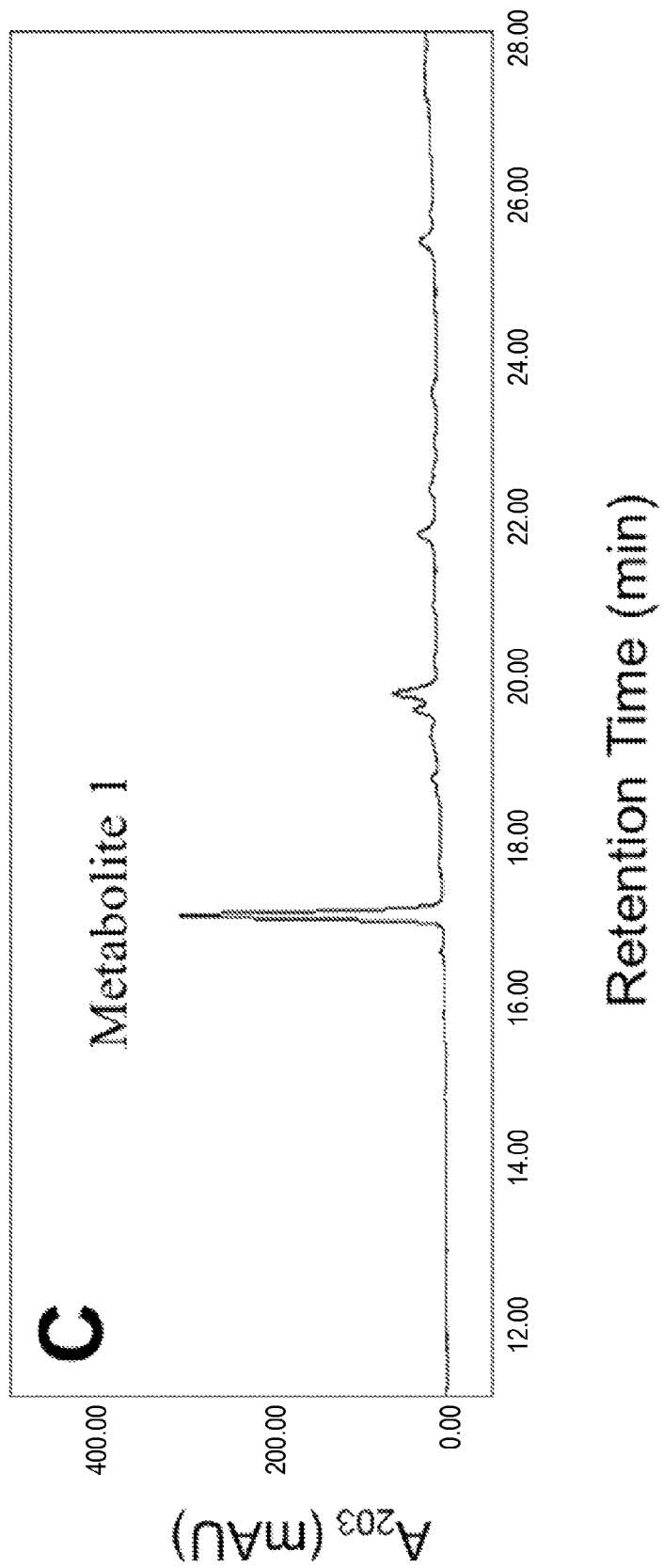
Figure 6:
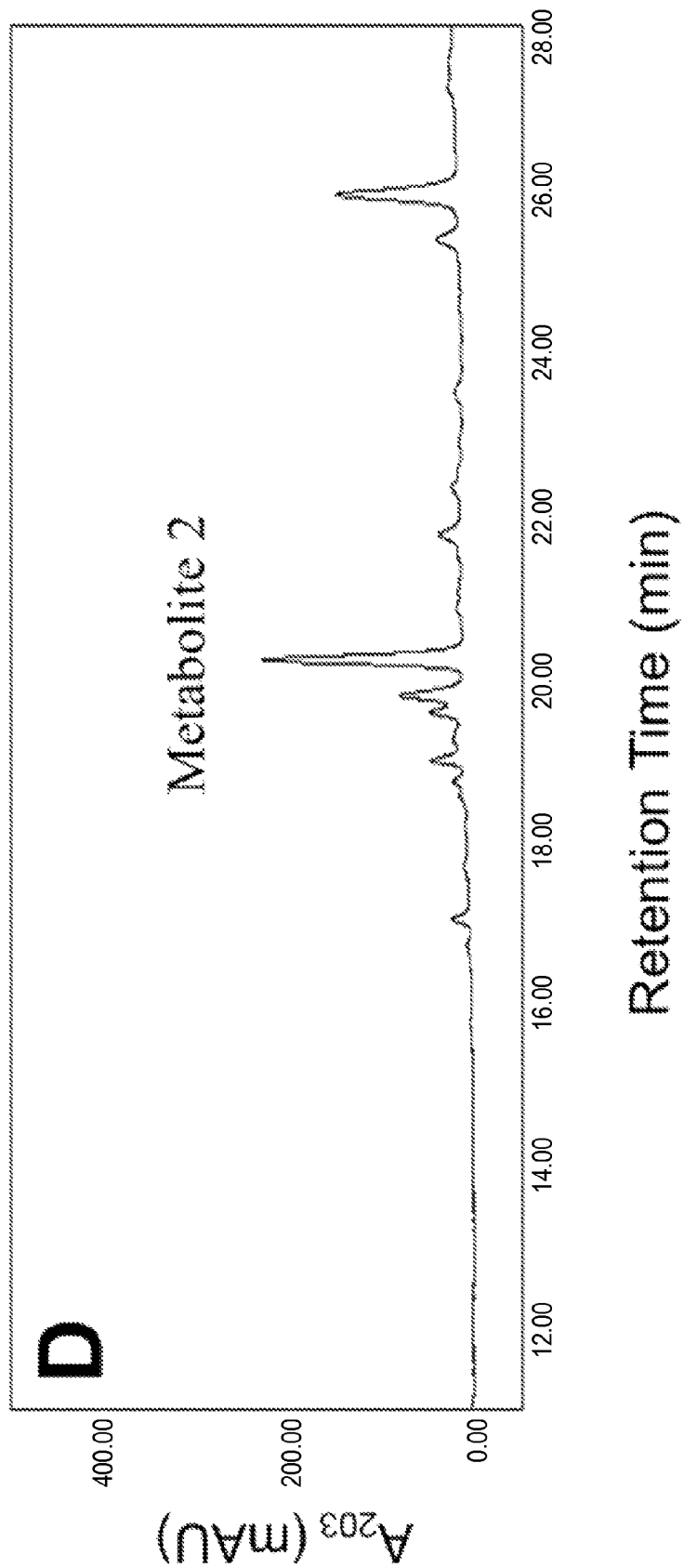
Figure 6:
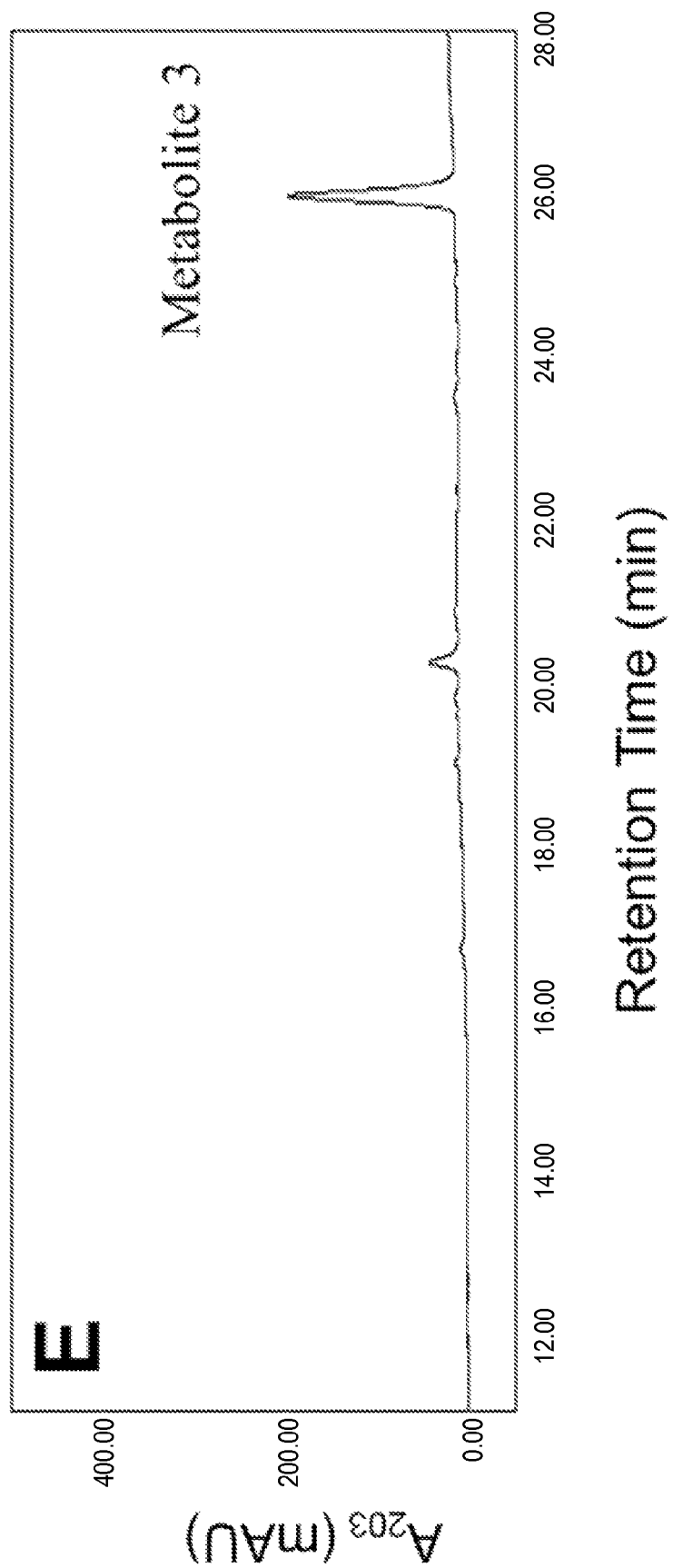
Figure 7:
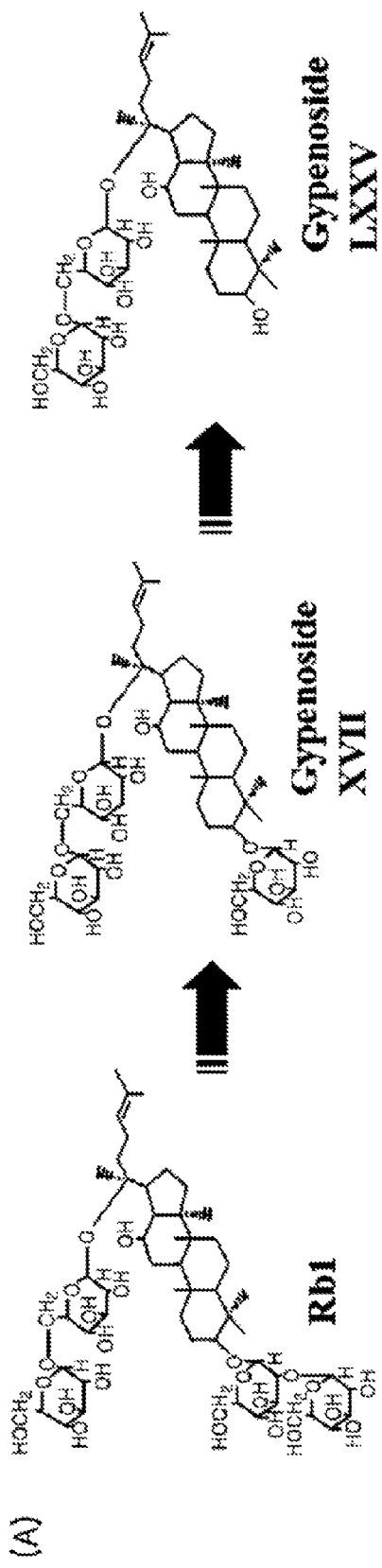
FIG. 7 is a schematic diagram showing bioconversion pathway of major ginsenosides Rb1, Rb2 and Rc by Bgl-gyp17.
Figure 7:
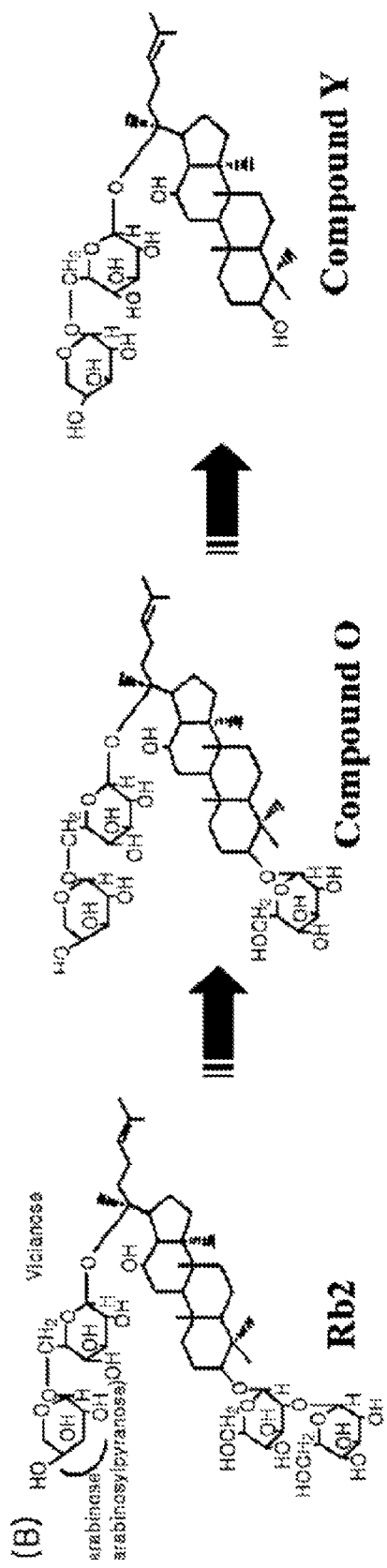
Figure 7:
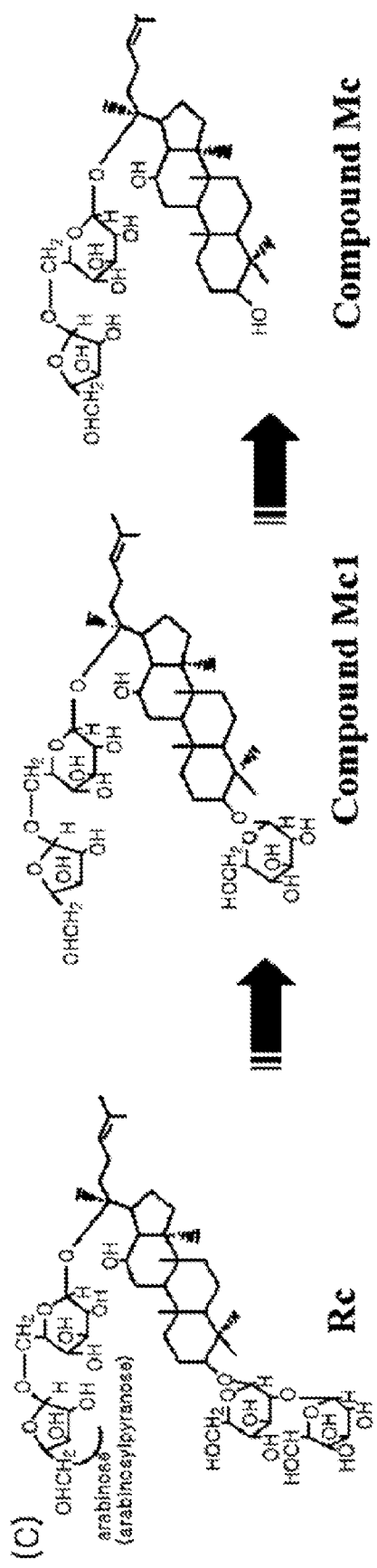

Purification of recombinant BGL-GYP17 resulted in 2.81-fold purification with a recovery of 9.3% from the inclusion body (Table 4). Gel filtration on Superose 6 10/300 GL (GE Healthcare) and SDS-PAGE showed that the natural ginsenoside glycosidase had a molecular weight of 56,000 and 64,000, respectively (FIG. 2). These results indicate that ginsenoside glycosidase is a monomeric protein.

Example 4

Enzyme Characterization

Specific activity was measured using 90 μl of 50 mM sodium phosphate buffer containing 2.0 mM pNPGlc (p-nitrophenyl-β-D-glucopyranoside; Sigma) at pH 7.0, and 10 μl of the diluted purified enzyme was treated at 37° C. for 20 minutes before initiation of the reaction, followed by incubation. 0.1 ml of 1 M $Na_2CO_3$ was treated for 5 minutes to terminate the reaction, and the secretion of p-nitrophenol was immediately measured at 405 nm. One unit of activity was defined as the amount of enzyme that released 1 μmol of p-nitrophenol per minute. Specific activity is expressed in units per milligram protein. Protein concentration was measured using a Bio-Rad protein staining reagent according to the protocol. All analyses were performed at least three times.

The pH effect on the enzymatic activity was measured using 2.0 mM pNPGlc in the following buffer (50 mM):

Buffer: pH range of 2 to 10: KCl—HCl (pH 2), glycine-HCl (pH 3), sodium acetic acid (pH 4 and 5), sodium phosphate (pH 6 and 7), Tris-HCl (pH 8 and 9) and glycine-sodium hydroxide (pH 10).

The enzyme was incubated in each of the above mentioned buffers at 4° C. for 24 hours, and then pHPGlc was analyzed in 50 mM potassium buffer to measure the enzymatic stability according to pH change. The activity was measured by the above mentioned method.

The results were represented as an activity probability obtained at the optimum pH.

The temperature-dependent activity in the 50 mM potassium phosphate buffer was analyzed within the temperature range of 4-90° C. using 2.0 mM pNPGlc at the optimum pH for 5 minutes. The equivalent amount of enzyme was incubated in 50 mM potassium phosphate buffer at different temperatures for 30 minutes to analyze the temperature stability. The sample was cooled in ice for 10 minutes, and the residual activity was measured by pNPGlc analysis.

The effects of metals and chemical agents were measured. Ginsenoside glycosidase was incubated at room temperature for 30 minutes in 1 mM and 10 mM (final concentration) of $HgCl_2$, $MnCl_2$, $CaCl_2$, $CoCl_2$, $MgCl_2$, EDTA, NaCl, KCl, $CuCl_2$, SDS, $ZnSO_4$, DTT and mercaptoethanol, and pNPGlc was used as a substrate to measure the activity. The resulting value was represented as a percentage of the obtained activity against that given a lack of the compounds.

1 activity unit was defined as the release of o-nitrophenol or p-nitrophenol per minute. For analysis of substrate preference, 2.0 mM chromogenic oNP and pNP (p-nitrophenyl) were used as the substrates, and incubated at 37° C. for 5 minutes. The analyzed substrates (Sigma) were pNP-β-D-glucopyranoside, pNP-β-D-galactopyranoside, pNP-β-D-fucopyranoside, pNP-β-D-glucosaminide, pNP-β-L-arabinopyranoside, pNP-β-D-mannopyronoside, pNP-β-D-xylopyranoside, pNP-α-D-glucopyranoside, pNP-α-L-arabinopyranoside, pNP-α-L-arabinopyranoside, pNP-α-D-rhamnopyranoside, pNP-α-D-mannopyranoside, pNP-α-D-xylopyranoside, o-nitrophenol[oNP]-β-D-glucopyranoside, oNP-β-D-galactopyranoside, oNP-β-D-fucopyranoside, and oNP-β-D-galactopyranoside.

Kinetic studies were performed with freshly purified enzyme using pNPGlc at the concentrations from 0.1 mM to 0.6 mM. Its absorbance at 405 nm was monitored at 37° C. for 20 minutes. The resulting data were used to determine Km and Vmax using the Enzyme Kinetics Program reported by Cleland.

Figure 8:
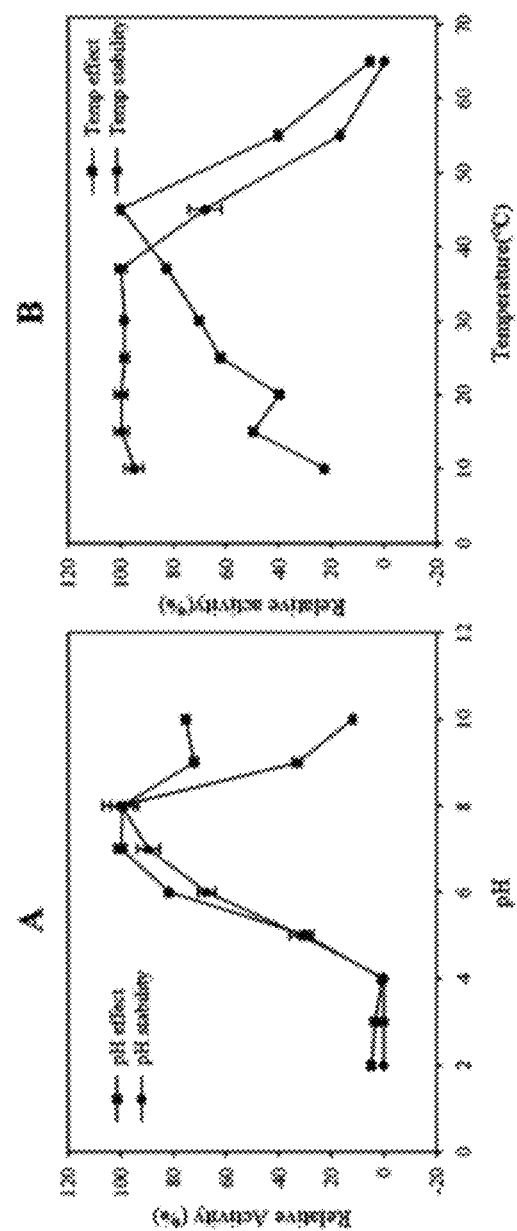
FIG. 8 shows the effects of pH (A) and temperature (B) on stability and activity of the recombinant Bgl-gyp17 purified from *E. coli*, in which the pH effect on the activity was examined using 2.0 mM pHPGlc in the following buffer (50 mM) of pH 2 to 10, buffer: KCl—HCl (pH 2), glycine-HCl (pH 3), sodium acetic acid (pH 4 and 5), sodium phosphate (pH 6 and 7), Tris-HCl (pH 8 and 9) and glycine-sodium hydroxide (pH 10).

As a result, Bgl-gyp 17 showed the maximum activity at 45° C. and pH 7.0 in sodium phosphate buffer. The enzyme was stabilized at 37° C. or lower, and lost approximately 32% of the activity after incubation at 45° C. for 30 minutes (FIG. 8).

The effects of various compounds on Bgl-gyp17 activity were shown in Table 5. The majority of the metal ions and chelating agents barely affected the enzymatic activity, but $Hg^{2+}$ ion strongly inhibited the activity, and SDS showed an inhibitory effect at the concentration of 10 mM or more. In order to examine the substrate specificity of Bgl-gyp17, it was incubated in 50 mM sodium phosphate buffer containing 2.0 mM βα and β-type p-NP (p-nitrophenyl) and oNP (O-nitrophenyl)-glycosidase at pH 7.0 and 37° C. As a result (Table 6), ginsenoside glycosidase showed the highest activity for oNP-β-D-glucopyranoside, followed by pNP-β-D-glucopyranoside, and was almost inert toward various pNP- or oNP-glycosides, with the exception of pNP- or oNP-β-D-fucopyranoside. The Km and Vmax for the hydrolysis of pNPGlc by ginsenoside glycosidase were determined using 0-2 mM substrate and the enzyme kinetics program reported by Cleland. The values measured by the program were 4.24 mM and 0.10 mmol*min$^{-1}$*mg of protein$^{-1}$ for pNpGlc.

TABLE 5

Effects of metal ions and chemical agents on purified recombinant BGL-GYP17 activity

| Metal ions or reagents | Relative activity[a] (%) | |
|---|---|---|
| | 1 mM | 10 mM |
| Nacl | 102.3 ± 5.15 | 97.7 ± 4.51 |
| KCl | 102.7 ± 4.65 | 96.2 ± 4.64 |
| MgCl2 | 94.8 ± 5.10 | 95.2 ± 5.14 |
| MnCl2 | 101.1 ± 5.45 | 96.9 ± 4.79 |
| CoCl2 | 100.9 ± 8.43 | 97.0 ± 5.04 |
| ZnCl2 | 92.8 ± 4.72 | 72.8 ± 4.27 |
| CaCl2 | 91.8 ± 4.59 | 101.5 ± 5.23 |
| CuCl2 | 84.7 ± 4.48 | 71.7 ± 5.07 |
| SDS | 94.8 ± 6.98 | 2.7 ± 3.22 |
| EDTA | 98.6 ± 6.49 | 96.6 ± 4.52 |
| Beta-Mercaptoethanol | 98.4 ± 4.89 | 102.5 ± 4.57 |
| DTT | 96.7 ± 5.59 | 96.6 ± 5.14 |
| Control | 100.0 ± 5.17 | 100.0 ± 5.11 |

[a]The specific activity at 100% was 44.3 U/mg.

TABLE 6

| Substrate | Relative activity[a] (%) |
|---|---|
| pNP-α-D-glucopyranoside | 1.12 ± 0.214 |
| pNP-α-D-mannopyranoside | 0 |
| pNP-α-D-xylopyranoside | 0 |
| pNP-α-L-arabinofuranoside | 0 |
| pNP-α-L-arabinopyranoside | 0 |
| pNP-α-L-rhamnopyranoside | 0 |
| pNP-β-D-fucopyranoside | 6.98 ± 0.063 |
| pNP-β-D-glactopyranoside | 0 |
| pNP-β-D-glucopyranoside | 89.52 ± 4.430 |
| pNP-β-D-glucosaminide | 0 |
| pNP-β-D-mannopyranoside | 0 |
| pNP-β-D-xylopyranoside | 0 |
| pNP-β-L-binopyranoside | 0 |
| oNP-α-D-galactopyranoside | 0 |
| oNP-β-D-fucopyranoside | 15.88 ± 0.544 |
| oNP-β-D-galatopyranoside | 2.33 ± 0.081 |
| oNP-β-D-glucopyranoside | 100.00 ± 3.542 |

[a]Activity on ONPGlu was taken as 100% and corresponds to a specific activity of 44.3 U/mg.

Example 5

Analysis on Enzymatic Hydrolysis of Ginsenoside

In order to analyze the specificity and selectivity of the recombinant enzyme for the hydrolysis of glucose at the C-3 and C-20 positions of PPD-type ginsenoside, ginsenoside Rb1, Rb2, Rc, Rd, and Rg3 were used as substrates. Each reaction mixture containing 0.2 U enzyme, 50 mM sodium phosphate buffer 0.1% (w/v) (pH 7.0), and the substrate was incubated at 37° C. Each sample was withdrawn at regular intervals, and an equal volume of water-saturated butanol was added to stop the reaction. The n-butanol fraction was evaporated to dryness, and any residual material was dissolved in $CH_3OH$ and then examined by TLC HPLC or NMR analysis.

The conversion step was dependent on the concentration of the reaction solution. 1 mg/ml of ginsenoside Rb1 was completely hydrolyzed to produce gyp XVII at the enzyme concentrations lower than 0.01 mg/ml. When ginsenoside Rb1 was 0.1 mg/ml, gypVXII could be subsequently converted into gyp LXXV. At enzyme concentrations of 1 mg/ml, Gyp LXXV started to appear at 10 min and reached a maximum level at 2 h, before gradually decreasing to an almost undetectable level at 24 h. Final product of compound K was produced at 24 h. These enzyme concentrations can be achieved through the refolding step by directly diluting 40 mM of the solubilized inclusion body in 50 mM phosphate buffer at pH 7.5.

Ginsenoside Rd was converted into F2 by cleavage of terminal glucose at the C-3 position of Rd, and subsequently, F2 was further converted into C—K (compound K) by cleavage of inner glucose at the C-3 position of F2.

When ginsenoside Rg3 was used as a substrate, the enzyme produced ginsenoside Rh2 by hydrolysis of terminal glucose at the C-3 position of Rg3, and further converted Rh2 into PPD by cleavage of inner glucose of Rh2.

In addition, the enzyme of the present invention converted ginsenoside Rb2 and Rc into C—Y (compound Y) and C-Mc (compound Mc) via C—O (compound O) and C-Mc1 (compound Mc1) by cleavage of terminal and inner glucoses at the C-3 position.

Consequently, the recombinant Bgl-gyp17 could convert ginsenoside Rb1, gyp XVII, and gyp LXXV into C—K; Rd and F2 into C—K; Rg3 and Rh2 into PPD; Rb2 and C—O into C—Y; and Rc and C-Mc1 into C-Mc by selective hydrolysis of terminal and inner glucoses at the C-3 position of PPD-type ginsenosides.

---

What is claimed is:

1. An isolated protein having ginsenoside glycosidase activity, consisting of SEQ ID NO: 1.

2. The protein according to claim 1, wherein the protein has an ability of selectively hydrolyzing the C-3 position of PPD (protopanaxadiol)-type saponin.

3. A composition for converting PPD-type saponins into in vivo absorbable saponins, comprising the protein of claim 1 as an active ingredient.

4. An isolated protein having ginsenoside glycosidase activity, comprising SEQ ID NO:1.

5. A composition for converting PPD-type saponins into in vivo absorbable saponins, comprising the protein of claim 4 as an active ingredient.

6. A method for converting PPD-type saponins into in-vivo absorbable, soluble saponins using the protein of claim 1.

7. The method according to claim 6, wherein the method is performed by hydrolysis at the C-3 position of PPD-type saponin.

8. The method according to claim 6, wherein the conversion into soluble saponins is one or more selected from the group consisting of conversion of ginsenoside Rb1 into gypenoside XVII, conversion of gypenoside XVII into gypenoside LXXV, conversion of gypenoside LXXV into compound K, conversion of ginsenoside Rb2 into compound Y, conversion of compound O into compound Y, conversion of ginsenoside Rc into compound Mc, and conversion of compound Mc1 into compound Mc.

9. The method according to claim 6, wherein the conversion is one or more selected from the group consisting of, converting ginsenoside Rd into compound K, converting ginsenoside F2 into compound K, converting ginsenoside Rg3 into PPD and converting of ginsenoside Rh2 into PPD.

* * * * *